United States Patent
Li et al.

(10) Patent No.: US 11,311,745 B2
(45) Date of Patent: Apr. 26, 2022

(54) SYSTEM AND METHOD FOR SYNCHRONOUS MOTION OPTIMIZATION OF DEVICE WITH MOVING COMPONENTS

(71) Applicant: SHANGHAI UNITED IMAGING HEALTHCARE CO., LTD., Shanghai (CN)

(72) Inventors: Zihan Li, Shanghai (CN); Supratik Bose, Concord, CA (US); Boqi Ma, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 654 days.

(21) Appl. No.: 16/234,235

(22) Filed: Dec. 27, 2018

(65) Prior Publication Data

US 2019/0201715 A1    Jul. 4, 2019

Related U.S. Application Data

(63) Continuation of application No. PCT/CN2017/120051, filed on Dec. 29, 2017.

(51) Int. Cl.
*A61N 5/10* (2006.01)
*G05D 3/20* (2006.01)

(52) U.S. Cl.
CPC ......... *A61N 5/1031* (2013.01); *A61N 5/1037* (2013.01); *A61N 5/1047* (2013.01);
(Continued)

(58) Field of Classification Search
CPC .. A61N 5/1031; A61N 5/1036; A61N 5/1037; A61N 5/1047; A61N 5/1048
See application file for complete search history.

(56) References Cited

U.S. PATENT DOCUMENTS

| 5,179,514 A | 1/1993 | Rastegar et al. |
| 6,216,058 B1 | 4/2001 | Hosek et al. |
| (Continued) | | |

FOREIGN PATENT DOCUMENTS

| CN | 1953782 A | 4/2007 |
| CN | 105455834 A | 4/2016 |
| (Continued) | | |

OTHER PUBLICATIONS

International Search Report in PCT/CN2017/120051 dated Sep. 29, 2018, 4 pages.
(Continued)

*Primary Examiner* — Christine H Matthews
(74) *Attorney, Agent, or Firm* — Metis IP LLC

(57) ABSTRACT

Systems and methods for synchronous motion optimization of device of moving components are provided. The methods may include obtaining positions of multiple components of a system; determining, based on the positions, a velocity of each component at each position; determining, based on the velocity of each component, a minimum duration for each component to traverse each segment between two sequential positions; determining, based on the minimum duration for each component to traverse each segment, an optimized duration corresponding to each segment; and determining, based on the optimized duration corresponding to each segment, motion parameters of each component in each segment, the motion parameters of each component in each segment forming the control plan of the system.

20 Claims, 15 Drawing Sheets

(52) U.S. Cl.
CPC ............. *A61N 5/1048* (2013.01); *G05D 3/20* (2013.01); *A61N 5/1036* (2013.01)

(56) References Cited

U.S. PATENT DOCUMENTS

| | | | |
|---|---|---|---|
| 7,130,716 | B2 | 10/2006 | Rogers et al. |
| 8,027,431 | B2 | 9/2011 | Stahl et al. |
| 8,290,611 | B2 | 10/2012 | Sladek et al. |
| 8,295,435 | B2 | 10/2012 | Wang et al. |
| 8,503,608 | B2 | 8/2013 | Brown et al. |
| 2004/0024300 | A1 | 2/2004 | Graf |
| 2004/0066882 | A1 | 4/2004 | Eberhard et al. |
| 2007/0222442 | A1 | 9/2007 | Aldefeld et al. |
| 2008/0123813 | A1 | 5/2008 | Maurer et al. |
| 2008/0226030 | A1 | 9/2008 | Otto |
| 2009/0225942 | A1 | 9/2009 | Shepard et al. |
| 2010/0046706 | A1 | 2/2010 | Moreau |
| 2010/0051824 | A1 | 3/2010 | Nord et al. |
| 2013/0216026 | A1 | 8/2013 | Nord et al. |
| 2013/0324784 | A1 | 12/2013 | Fredriksson |
| 2015/0335914 | A1 | 11/2015 | Otto |
| 2017/0203125 | A1 | 7/2017 | Amato et al. |
| 2017/0354393 | A1 | 12/2017 | Bose et al. |
| 2018/0111007 | A1 | 4/2018 | Gordon et al. |
| 2019/0175940 | A1 | 6/2019 | Hissoiny et al. |

FOREIGN PATENT DOCUMENTS

| | | |
|---|---|---|
| CN | 105892402 A | 8/2016 |
| CN | 105999567 A | 10/2016 |
| CN | 106113034 A | 11/2016 |

OTHER PUBLICATIONS

Written Opinion in PCT/CN2017/120051 dated Sep. 29, 2018, 4 pages.
First Office Action in Chinese Application No. 201811629517.1 dated Apr. 15, 2020, 19 pages.
First Office Action in Chinese Application No. 201710434391.1 dated Mar. 22, 2019, 21 pages.
The Extended European Search Report in European Application No. 17178521.5 dated Oct. 13, 2017, 9 pages.
Otto K., Volumetric Modulated Arc Therapy: IMRT in a Single Gantry Arc, Medical Physics, 35(1): 310-317, 2008.
Kjaer-Kristoffersen F et al., RapidArc Volumetric Modulated Therapy Planning for Prostate Cancer Patients, Acta Oncologica, 48: 227-232, 2009.
Bedford J. L., Treatment Planning for Volumetric Modulated Arc Therapy, Medical Physics, 36(11): 5128-5138, 2009.
Bill J Salter et al., Rotational IMRT Delivery Using a Digital Linear Accelerator in Very High Dose Rate Burst Mode, Medical Physics, 56: 1931-1946, 2011.
Calippe Serge, RapidArc Workshop Session 1(a), RapidArc Workshop, 2012, 96 pages.
D. Rangaraj et al., Fundamental Properties of the Delivery of Volumetric Modulated Arc Therapy (VMAT) to Static Patient Anatomy, Medical Physics, 37(8): 4056-4067, 2010.
Lin, Chun-Shin et al., Formulation and Optimization of Cubic Polynomial Joint Trajectories for Industrial Robots, IEEE Transactions on Automatic Control, 28(12): 1066-1074, 1983.
Wang, Chi-Hsu et al., Constrained Minimum-time Path Planning for Robot Manipulators via Virtual Knots of the Cubic B-spline Functions, IEEE Transactions on Automatic Control, 35(5): 573-577, 1990.
Kruger CJC, Constrained Cubic Spline Interpolation for Chemical Engineering Applications, 2003, 5 pages.
Biagiotti Luigi, et al., Trajectory Planning for Automatic Machine and Robots, Springer Verlag, 2008, 513 pages.
Iravani P. et al., Variable-Velocity Exponential Input Shaping for Position Controlled Robotic Systems, Proceedings of the ASME 2010 Dynamic Systems and Control Conference, 2010, 7 pages.
Rymansaib, Z. et al., Exponential Trajectory Generation for Point to Point Motions, 2013 IEEE/ASME International Conference on Advanced Intelligent Mechatronics (AIM), 906-911, 2013.
Konar T. S. et al., Integration of $e^{\wedge}(x^{\wedge}n)$ and $e^{\wedge}(-x^{\wedge}n)$ in Forms of Series, Their Applications in the Field of Differential Equation; Introducing Generalized Form of Skewness and Kurtosis; Extension of Starling's Approximation, Eprint arXiv:0803.2736, 2008, 19 pages.
Wijesooriya K. et al., Determination of Maximum Leaf Velocity and Acceleration of a Dynamic Multileaf Collimator Implications for 4D Radiotherapy, Medical Physics, 32(4): 932-941, 2005.
Song Y. et al., Dosimetric Effects of Gantry Angular Acceleration and Deceleration in Volumetric Modulated Radiation Therapy, International Federation for Medical and Biological Engineering (IFMBE) Proceedings, 25: 1046-1050, 2009.
International Electrotechnical Commission. Radiotherapy Equipment Coordinates, Movements and Scales, International Standard, IEC 61217 Edition 2.0, 2002, 19 pages.
National Electrical Manufacturers Association. Digital Imaging and Communications in Medicine (DICOM) part 3: Information object definitions. 2007, 27 pages.
Amendola B. E. et al., Volumetric-Modulated Arc Therapy with RapidArc: An Evaluation of Treatment Delivery Efciency, Reports of Practical Oncology and Radiotherapy, 18: 383-386, 2013.

| Control nodes | Dose/MU | Gantry° | MLC shape (120 leaf) |
|---|---|---|---|
| $CP_0$ | 0 | 0 | Shape 0 |
| $CP_1$ | 0.8 | 2 | Shape 1 |
| $CP_2$ | 2.1 | 4 | Shape 2 |
| ... | ... | ... | ... |
| $CP_{n-1}$ | 418.5 | 358 | Shape m-1 |
| $CP_m$ | 420 | 360 | Shape m |

FIG. 9

SYSTEM AND METHOD FOR SYNCHRONOUS MOTION OPTIMIZATION OF DEVICE WITH MOVING COMPONENTS

CROSS-REFERENCE TO RELATED APPLICATIONS

This application is a continuation of International Application No. PCT/CN2017/120051, filed on Dec. 29, 2017. The entire contents of the application are incorporated herein by reference.

TECHNICAL FIELD

The present disclosure generally relates to synchronous motion optimization, and more particularly to a system and method for optimizing synchronous motions of multiple components in a radiotherapy apparatus or system.

BACKGROUND

Contemporary radiotherapy systems may provide specialized treatment by delivering radiation doses, e.g., personalized radiation doses. During a treatment process, multiple components such as a gantry, a collimator, one or more leaves of a multi-leaf collimator, a table may move synchronously with the delivery of a radiation dose. This process may be time-consuming, and may lead to a large amount of radiation dose delivered to a patient. Thus, there is a need for a system and method to optimize the synchronous motions of the multiple components as well as the delivery of a radiation dose to reduce the treatment time and the radiation exposure to a patient.

SUMMARY

In some aspects of the present disclosure, a method implemented on at least one device each of which has at least one processor and a storage device is provided. The method may include one or more of the following operations. A plurality of sets of positions of multiple components of an apparatus may be obtained, each set of positions of the multiple components corresponding to a control node, and two sequential controls defining a segment. A velocity of each component at each control node may be determined based on the plurality of sets of positions of the multiple components. A minimum duration for each component to traverse each segment of the at least one segment may be determined based on the velocity of each component at each control node. An optimized duration corresponding to each segment may be determined based on the minimum duration for each component to traverse each segment of the at least one segment. Motion parameters of each component in each segment may be determined based on the optimized duration corresponding to each segment.

In some embodiments, the motion parameters may be such that the multiple components moving according to the motion parameters arrive at positions defined by a control node at a same time.

In some embodiments, the apparatus may include a radiotherapy device, the multiple components including at least one of a gantry, one or more leaves of a multi-leaf collimator (MLC), or a radiation dose.

In some embodiments, the method may further include delivering the radiation dose during the at least one segment based on the plurality of sets of positions of the multiple components.

In some embodiments, the motion parameters of each component may include at least one of an acceleration duration, a cruise duration, a deceleration duration, or a cruise velocity.

In some embodiments, the determination of a velocity of each component at each control node based on the plurality of sets of positions of the multiple components may include one or more of the following operations. For each component at a current control node, a first displacement between a reference control node and a prior control node may be determined based on the plurality of sets of positions of the multiple components. A second displacement between the reference control node and the current control node may be determined based on the plurality of sets of positions of the multiple components. A third displacement between the reference control node and a subsequent control node may be determined based on the plurality of sets of positions of the multiple components. The velocity of the component at the current control node may be determined based on the first displacement, the second displacement, and the third displacement.

In some embodiments, the determination of the velocity of the component at the current control node based on the first displacement, the second displacement, and the third displacement may include one or more of the following operations. Determining that the first displacement, the second displacement, and the third displacement fail to conform to a monotonic change with time. In response to a determination that the first displacement, the second displacement, and the third displacement fail to conform to a monotonic change with time, the velocity of the component at the current control node may be designated as zero. Determining that the first displacement, the second displacement, and the third displacement conform to a monotonic change with time. In response to a determination that the first displacement, the second displacement, and the third displacement conform to a monotonic change with time, the velocity of the component at the current control node may be designated as non-zero.

In some embodiments, the determination of the minimum duration for each component to traverse each segment of the at least one segment may include one or more of the following operations. For each component in each segment of the at least one segment, a set of motion constraints of the component may be obtained. A velocity mode of the component may be determined based on the velocity of the component at each control node. The minimum duration for the component to traverse the segment may be determined based on the velocity mode and the set of motion constraints.

In some embodiments, the velocity mode includes an acceleration-cruise-deceleration mode, an acceleration-cruise mode, a cruise-deceleration mode, or a cruise mode.

In some embodiments, the determination of the optimized duration corresponding to each segment based on the minimum duration for each component to traverse each segment of the at least one segment may include one or more of the following operations. For the each segment of the at least one segment, a candidate minimum duration corresponding to the each segment may be determined based on the minimum duration for each component to traverse the each segment. The optimized duration corresponding to the each segment may be determined based on the at least one candidate minimum duration corresponding to the each segment.

In some embodiments, the determination of the optimized duration corresponding to each segment based on the minimum duration for each component to traverse each segment of the at least one segment may further include: for the each segment of the at least one segment, determining a candidate maximum duration corresponding to the each segment based on the minimum duration for each component to traverse the each segment, the candidate maximum duration and the candidate minimum duration constitute a range within which the optimized duration is determined.

In some embodiments, the determination of the optimized duration corresponding to each segment may further include the one or more of the following operations. Entry velocities of the multiple components at a starting control node and exit velocities of the multiple components at an ending control node of the segment may be determined based on the at least one candidate minimum duration corresponding to the at least one segment. Maximum effective displacements of the multiple components in the segment may be determined based on the entry velocities and the exit velocities in the segment. Displacements of the multiple components in the segment may be determined based on the plurality of sets of positions of the multiple components. The optimized duration corresponding to the segment may be determined based on the maximum effective displacements and the displacements of the multiple components.

In some embodiments, the determination of the optimized duration corresponding to each segment may further include the one or more of the following operations. Determining that the displacements of the multiple components are smaller than the maximum effective displacements. In response to a determination that the displacements of the multiple components are smaller than the maximum effective displacements, the candidate minimum duration may be designated as the optimized duration for the segment.

In some embodiments, the determination that the displacements of the multiple components are smaller than the maximum effective displacements may further include the one or more of the following operations. Determining that the displacements of the multiple components are between the maximum effective displacements and minimum effective displacements, the minimum effective displacements are displacements that the multiple components reach within the candidate minimum duration.

In some embodiments, the determination of the optimized duration corresponding to each segment may further include the one or more of the following operations. Determining that at least one of the displacements of the multiple components is larger than the maximum effective displacement. In response to a determination that at least one of the displacements of the one or more components is larger than the maximum effective displacement, the candidate minimum duration corresponding to the segment may be updated in one or more iterations.

In some embodiments, the each of the one or more iterations may further include updating the candidate minimum duration based on the displacements of the multiple components, the minimum effective displacements of the multiple components, and the maximum effective displacements of the multiple components.

In some embodiments, the determination of the optimized duration corresponding to each segment may further include identifying one or more components from the multiple components, the one or more iterations for the determination of the optimized duration are performed with respect to the identified one or more components prior to the other components.

In some embodiments, the identified one or more components may include a first component with a larger minimum duration compared to other components of the multiple components, a first leaf of an MLC with a larger displacement in a first motion mode compared to other components of the multiple components, a second leaf of the MLC with a larger displacement in a second motion mode compared to other components of the multiple components, and a third leaf of the MLC with a larger displacement in a third motion mode compared to other components of the multiple components.

In some embodiments, the determination of the optimized duration corresponding to the segment may further include one or more of the following operations. Determining that at least one of the displacements of the one or more components is larger than the maximum effective displacement. In response to a determination that at least one of the displacements of the one or more components is larger than the maximum effective displacement, the optimized duration corresponding to another segment occurred prior to the segment in time may be determined.

In some embodiments, the determination of the optimized duration corresponding to the segment may further include performing the determination of the optimized duration for a second segment after the optimized duration for a first segment is determined, the first segment being prior to the second segment in time.

In another aspect of the present disclosure, a system for rapid trajectory optimization is provided. The system may include at least one processor and a storage device. The storage device may store instructions. The instructions, when executed by the at least one processor, may cause the system to perform one or more of the following operations. A plurality of sets of positions of multiple components of an apparatus may be obtained, each set of positions of the multiple components corresponding to a control node, and two sequential controls defining a segment. A velocity of each component at each control node may be determined based on the plurality of sets of positions of the multiple components. A minimum duration for each component to traverse each segment of the at least one segment may be determined based on the velocity of each component at each control node. An optimized duration corresponding to each segment may be determined based on the minimum duration for each component to traverse each segment of the at least one segment. Motion parameters of each component in each segment may be determined based on the optimized duration corresponding to each segment.

In a further aspect of the present disclosure, a system for rapid trajectory optimization is provided. The system may include an acquisition module and processing module. The acquisition module may be configured to obtain a plurality of sets of positions of multiple components of an apparatus, each set of positions of the multiple components corresponding to a control node, and two sequential controls defining a segment. The processing module may include a velocity determination unit, a duration determination unit, and a motion parameter determination unit. The velocity determination unit may be configured to determine a velocity of each component at each control node based on the plurality of sets of positions of the multiple components. The duration determination unit may be configured to determine a minimum duration for each component to traverse each segment of at least one segment based on the velocity of each component at each control node, and determine an optimized duration corresponding to each segment based on the minimum duration for each component to traverse each segment of the at least one segment. The motion parameter determination unit may be configured to determine motion parameters of each component in each segment based on the optimized duration corresponding to each segment.

In yet another aspect of the present disclosure, a non-transitory computer readable medium is provided. The non-transitory computer readable medium storing instructions, the instructions, when executed by a computer, may cause the computer to implement a method. The method may include one or more of the following operations. A plurality of sets of positions of multiple components of an apparatus may be obtained, each set of positions of the multiple components corresponding to a control node, and two sequential controls defining a segment. A velocity of each component at each control node may be determined based on the plurality of sets of positions of the multiple components. A minimum duration for each component to traverse each segment of the at least one segment may be determined based on the velocity of each component at each control node. An optimized duration corresponding to each segment may be determined based on the minimum duration for each component to traverse each segment of the at least one segment. Motion parameters of each component in each segment may be determined based on the optimized duration corresponding to each segment.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 9 illustrates exemplary plan data according to some embodiments of the present disclosure;

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by other expression if they achieve the same purpose.

Figure 2:
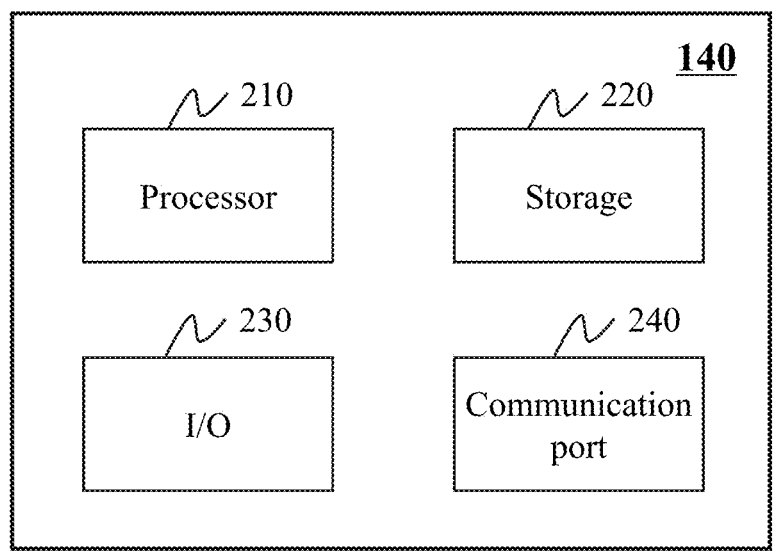
FIG. 2 is a schematic diagram illustrating exemplary hardware and/or software components of an exemplary computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in a firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems with multiple moving components for medical or industrial application, such as for disease treatment, disease diagnosis, synchronous motion control, research purposes, etc. In some embodiments, the system may be a radiotherapy (RT) system, a computed tomography (CT) system, an ultrasonography system, an X-ray photography system, or the like, or any combination thereof. The following descriptions are provided with reference to an RT system for illustration purposes and not intended to limit the scope of the present disclosure.

In an aspect, the present disclosure is directed to systems and methods for synchronous motion optimization. Position information of multiple components in a radiotherapy system may be used to determine a duration during which the multiple components motion synchronously from one position to another. The duration may be optimized in a plurality of iterations to decrease the length of the duration.

Figure 1:
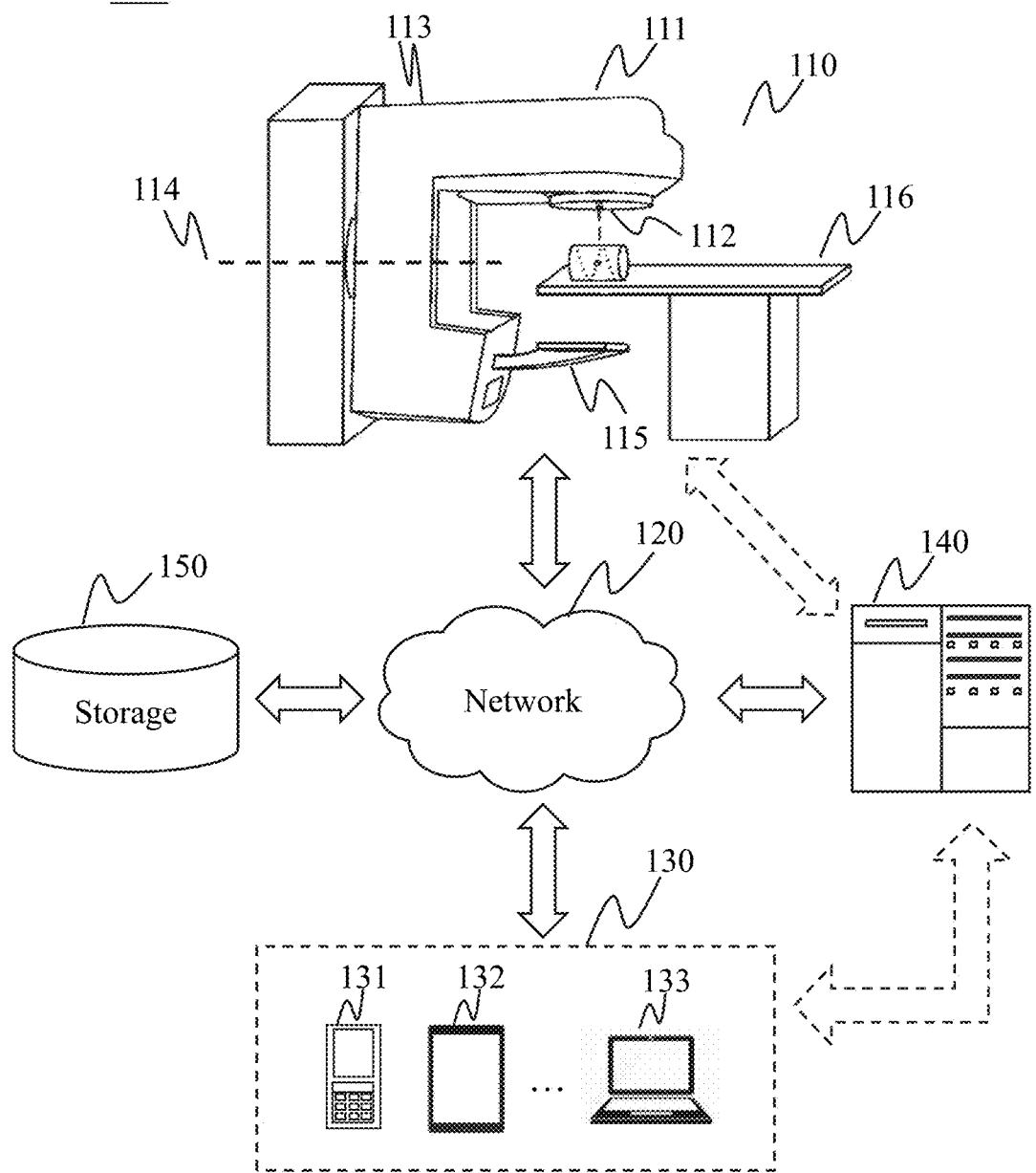
FIG. 1 is a schematic diagram illustrating an exemplary radiotherapy system according to some embodiments of the present disclosure.

FIG. 1 is a schematic diagram illustrating an exemplary radiotherapy system according to some embodiments of the present disclosure. As shown in FIG. 1, the radiotherapy system 100 may include a radiotherapy device 110, a network 120, one or more terminals 130, a processing device 140, and storage 150.

The radiotherapy device 110 may deliver a radiation beam to a target object (e.g., a patient, or a phantom). In some embodiments, the radiotherapy device 110 may include a linear accelerator (also referred to as "linac") 111. The linac 111 may generate and emit a radiation beam (e.g., an X-ray beam) from a treatment head 112. The radiation beam may go through one or more collimators (e.g., a multi-leaf collimator (MLC)) of certain shapes, and enter into the target object. In some embodiments, the radiation beam may include electrons, photons, or other types of radiation. In some embodiments, the energy of the radiation beam may be in the megavoltage range (e.g., >1 MeV), and may therefore be referred to as megavoltage beam. The treatment head 111 may be coupled to a gantry 113. The gantry 113 may rotate, for example, clockwise or counter-clockwise around a gantry rotation axis 114. The treatment head 112 may rotate along with the gantry 113. In some embodiments, the radiotherapy device 110 may include an imaging element 115. The imaging element 115 may receive the radiation beam that passes through the target object, and generate images of patients and/or phantoms before, during and/or after a radiation treatment or a correction process based on received radiation beam. The imaging element 115 may include an analog detector, a digital detector, or the like, or a combination thereof. The imaging element 115 may be connected to the gantry 113 in any connection means, including an extendible housing. Thus, the rotation of the gantry 113 may cause the treatment head 112 and the imaging element 115 to rotate in a coordinated manner. In some embodiments, the radiotherapy device 110 may also include a table. A table 116 may support a patient during a radiation treatment or imaging, and/or support a phantom during a correction process of the radiotherapy device 110. The table may be adjustable to suit for different application scenarios.

The network 120 may include any suitable network that can facilitate exchange of information and/or data for the radiotherapy system 100. In some embodiments, one or more components of the radiotherapy system 100 (e.g., the radiotherapy device 110, the terminal 130, the processing device 140, the storage 150, etc.) may communicate information and/or data with one or more other components of the radiotherapy system 100 via the network 120. For example, the processing device 140 may obtain plan data from the terminal 130 via the network 120. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the radiotherapy system 100 may be connected to the network 120 to exchange data and/or information.

The terminal(s) 130 may enable interactions between a user and the radiotherapy system 100. The terminal(s) 130 may include a mobile apparatus 131, a tablet computer 132, a laptop computer 133, or the like, or any combination thereof. In some embodiments, the mobile apparatus 131 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™ etc. In some embodiments, the terminal(s) 130 may be part of the processing device 140.

The processing device 140 may process data and/or information obtained from the radiotherapy device 110, the terminal 130, and/or the storage 150. For example, the processing device 140 may process plan data, and determine motion parameters that may be used to control the motions of multiple components in the radiotherapy device 110. In some embodiments, the processing device 140 may be a computer, a user console, a single server or a server group, etc. The server group may be centralized or distributed. In some embodiments, the processing device 140 may be local or remote. For example, the processing device 140 may access information and/or data stored in the radiotherapy device 110, the terminal 130, and/or the storage 150 via the network 120. As another example, the processing device 140 may be directly connected to the radiotherapy device 110, the terminal 130, and/or the storage 150 to access stored information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented by a computing device 200 having one or more components as illustrated in FIG. 2.

The storage 150 may store data, instructions, and/or any other information. In some embodiments, the storage 150 may store data obtained from the terminal 130 and/or the processing device 140. In some embodiments, the storage 150 may store data and/or instructions that the processing device 140 may execute or use to perform exemplary methods described in the present disclosure. In some embodiments, the storage 150 may include a mass storage, a removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage 150 may be connected to the network 120 to communicate with one or more other components in the radiotherapy system 100 (e.g., the processing device 140, the terminal 130, etc.). One or more components in the radiotherapy system 100 may access the data or instructions stored in the storage 150 via the network 120. In some embodiments, the storage 150 may be directly connected to or communicate with one or more other components in the radiotherapy system 100 (e.g., the processing device 140, the terminal 130, etc.). In some embodiments, the storage 150 may be part of the processing device 140. In some embodiments, the processing device 140 may be connected to or communicate with the radiotherapy device 110 via the network 120, or at the backend of the processing device 140.

FIG. 2 is a schematic diagram illustrating exemplary hardware and/or software components of an exemplary computing device 200 on which the processing device 140 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (e.g., program code) and perform functions of the processing device 140 in accordance with techniques described herein. The computer instructions may include, for example, routines, programs, objects, components, data structures, procedures, modules, and functions, which perform particular functions described herein. For example, the processor 210 may process plan data obtained from the terminal 130, the storage 150, and/or any other component of the radiotherapy system 100. For example, the plan data may be obtained from a treatment planning system (TPS) associated with the radiotherapy system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, thus operations and/or method steps that are performed by one processor as described in the present disclosure may also be jointly or separately performed by the multiple processors. For example, if in the present disclosure the processor of the computing device 200 executes both step A and step B, it should be understood that step A and step B may also be performed by two or more different processors jointly or separately in the computing device 200 (e.g., a first processor executes step A and a second processor executes step B, or the first and second processors jointly execute steps A and B).

The storage 220 may store data/information obtained from the radiotherapy device 110, the terminal 130, the storage 150, and/or any other component of the radiotherapy system 100. In some embodiments, the storage 220 may include a mass storage, a removable storage, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RANI (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for determining motion parameters.

The I/O 230 may input and/or output signals, data, information, etc. In some embodiments, the I/O 230 may enable a user interaction with the processing device 140. In some embodiments, the I/O 230 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The communication port 240 may be connected to a network (e.g., the network 120) to facilitate data communications. The communication port 240 may establish connections between the processing device 140 and the radiotherapy device 110, the terminal 130, and/or the storage 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
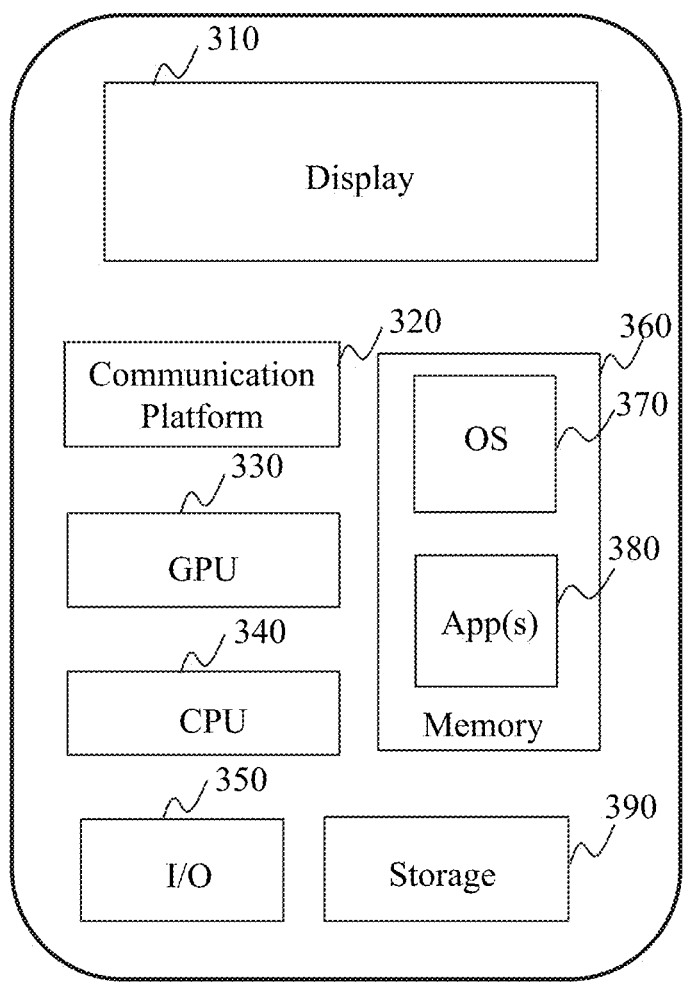
FIG. 3 is a schematic diagram illustrating exemplary hardware and/or software components of an exemplary mobile device according to some embodiments of the present disclosure.

FIG. 3 is a schematic diagram illustrating exemplary hardware and/or software components of an exemplary mobile device 300 on which the terminal 130 may be implemented according to some embodiments of the present disclosure. As illustrated in FIG. 3, the mobile device 300 may include a communication platform 310, a display 320, a graphic processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the radiotherapy system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4:
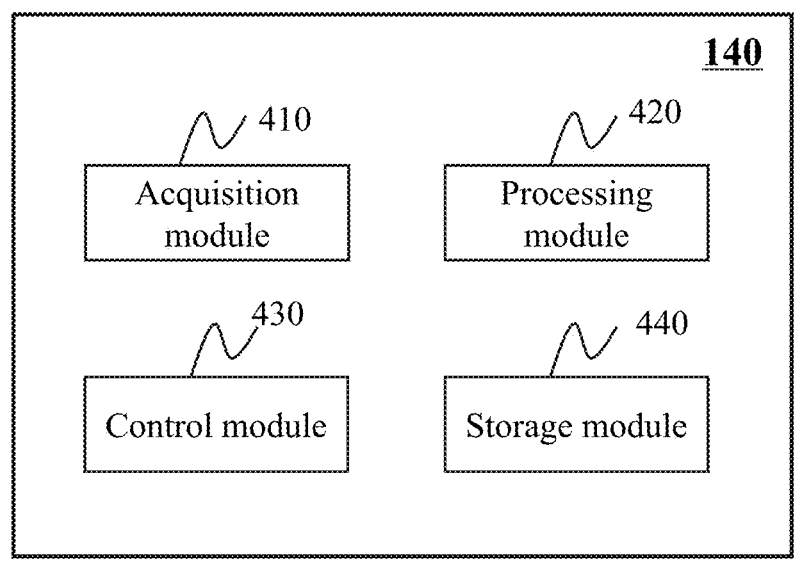
FIG. 4 is a block diagram illustrating an exemplary processing device according to some embodiments of the present disclosure.

FIG. 4 is a block diagram illustrating an exemplary processing device 140 according to some embodiments of the present disclosure. The processing device 140 may include an acquisition module 410, a processing module 420, a control module 430, and a storage module 440.

The acquisition module 410 may acquire data. The acquisition module 410 may acquire data from one or more of the radiotherapy device 110, the network 120, the terminal 130, the storage 150, or any devices or components disclosed in the present disclosure capable of storing data. The acquired data may include positions of multiple components, user instructions, algorithms, or the like, or a combination thereof. In some embodiments, the positions of the multiple components may include a plurality of sets of positions on trajectories of the multiple components. In some embodiments, each set of positions of the multiple components may correspond to a control node. The control node may relate to a time point at which the multiple components reach the set of positions, respectively. In some embodiments, two sequential control nodes may define a segment. In some embodiments, the positions of the multiple components may be determined according to plan data. The plan data may refer to data relating to a plan (e.g., a radiation treatment plan, a scanning plan, etc.). The plan data may include a plurality of discrete control nodes. For a radiation treatment plan, each control node of the plan data may include position information of multiple components at a time point, as well as a cumulative radiation dose delivered within a time period (e.g., a treatment session). The multiple components may include, for example, the gantry 113, one or more leaves of the MLC, the table 116, etc. In some embodiments, the position information may be used to determine motion parameters of the multiple components. In some embodiments, the radiation dose may be used to determine a dose rate at which the radiotherapy device 110 delivers the radiation dose. As used herein, a dose rate may refer to a radiation dose delivered in a unit time. In some embodiments, the radiation dose may be regarded as a component of the multiple components in the radiotherapy system 100. In some embodiments, a transition between two sequential control nodes, that is the transition from one control node to the subsequent control node, may be defined as a segment. In some embodiments, the plan data may include at least one segment.

In some embodiments, the acquisition module 410 may retrieve information, e.g., position information, velocity information, time, from a sensor. Exemplary sensors may include a position sensor, an angular position sensor, a timer, a velocity sensor, an acceleration sensor, etc. For instance, to control the motion of multiple components in a radiotherapy session based on motion parameters determined based on plan data, the acquisition module 410 may acquire real-time information (e.g., real-time positions, real-time velocities, real-time accelerations of one or more components, etc.), and feed the real-time information to the control module 430 to control or adjust the motion of the one or more components during the radiotherapy session.

In some embodiments, the acquisition module 410 may store the acquired data in the storage 150 and/or the storage module 440. In some embodiments, the acquisition module 410 may transmit the acquired plan data to a computing device (e.g., the processing module 420) for determining motion parameters of the multiple components, or a control device (e.g., the control module 430) for controlling motions of the multiple components.

The processing module 420 may process data provided by various modules of the processing device 140. For example, the processing module 420 may process the plan data acquired by the acquisition module 410, or retrieved from the storage module 440. The processing module 440 may process the obtained data by determining a plurality of parameters or values related to the plan data. For example, the processing module 420 may determine a velocity of a component at a control node, a duration for each component of multiple components to traverse a segment, and/or motion parameters of the multiple components of the apparatus (e.g., the radiotherapy device 110 with or without an imaging element). The motion parameters may be used to control the motions of the multiple components. In some embodiments, the processing module 420 may transmit the motion parameters of the multiple components to the control module 430 for controlling the motions of the multiple components.

The control module 430 may control operations of modules or components of the radiotherapy system 100. In some embodiments, the control module 430 may receive the motion parameters from the processing module 420, and control the motions of multiple components based on the motion parameters. The motions of the multiple components may include, for example, a linear motion, a reciprocating motion, a circular motion, or the like, or a combination thereof. In some embodiments, the control module 430 may include a position control unit and a velocity control unit. The position control unit may be configured to control positions of a component at a plurality of control nodes based on a trajectory curve of the component. In some embodiments, the trajectory curve may be determined based on the motion parameters, the mechanical structure of the radiotherapy device 110, or the like, or a combination thereof. Details regarding the position control unit may be found elsewhere in the present disclosure. See, for example, FIG. 15 and the descriptions thereof. The velocity control unit may be configured to control velocities of a component at a plurality of control nodes based on a velocity curve of the component. In some embodiments, the velocity curve may be determined based on the motion parameters.

The storage module 440 may store data. In some embodiments, the storage 440 may store one or more programs and/or instructions that may be executed by the processor(s) of the processing device 140 to perform exemplary methods described in this disclosure. For example, the storage 440 may store program(s) and/or instruction(s) that can be executed by the processor(s) of the processing device 140 to determine velocities of the multiple components, minimum duration for each component to traverse a segment, an optimized duration corresponding to a segment, and/or motion parameters of the multiple components.

In some embodiments, one or more modules illustrated in FIG. 4 may be implemented in at least part of the radiotherapy system 100 as illustrated in FIG. 1. For example, the acquisition module 410, the processing module 420, the control module 430, and/or the storage module 440 may be integrated into a console (not shown). Via the console, a user may set parameters for implementing operations (e.g., the plan data for treating a patient) described elsewhere in the present disclosure. In some embodiments, the console may be implemented via the processing device 140 and/or the terminal 130.

It should be noted that the above description is merely provided for the purposes of illustration, and not intended to limit the scope of the present disclosure. For persons having ordinary skills in the art, multiple variations or modifications may be made under the teachings of the present disclosure. For example, the processing device 140 may further include an I/O module for facilitating interactions between the radiotherapy system 100 and a user. However, those variations and modifications do not depart from the scope of the present disclosure.

Figure 5:
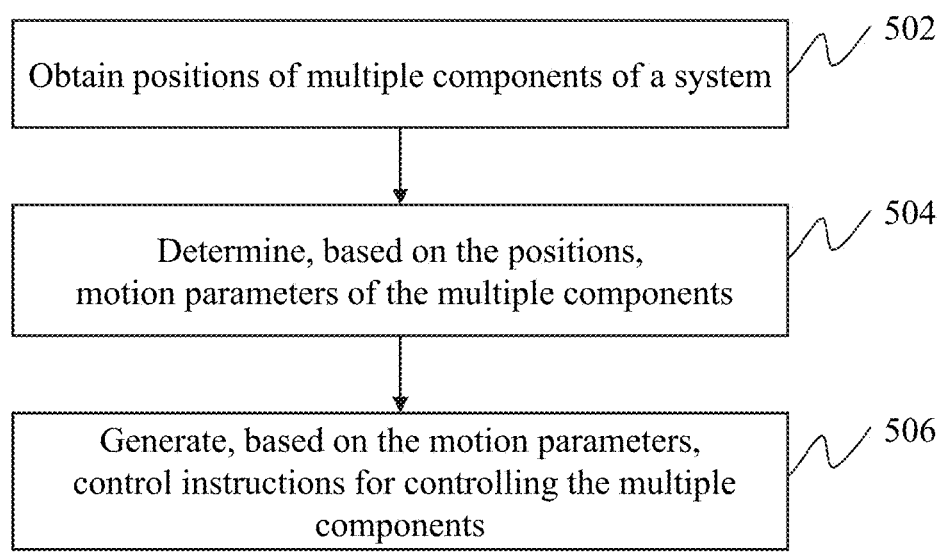
FIG. 5 is a flowchart illustrating an exemplary process for generating control instructions for controlling motions of multiple components according to some embodiments of the present disclosure.

FIG. 5 is a flowchart illustrating an exemplary process 500 for generating control instructions for controlling motions of multiple components according to some embodiments of the present disclosure. The process 500 and the other processes described herein may be performed using any suitable combination of hardware, software or manual means. Software embodying these processes may be stored by any non-transitory tangible medium, including a fixed disk, a floppy disk, a CD, a DVD, a Flash drive, or a magnetic tape.

In 502, positions of multiple components of a system may be obtained. The positions may be obtained by, for example, the acquisition module 410. In some embodiments, the positions of the multiple components may include a plurality of sets of positions on trajectories of the multiple components. In some embodiments, each set of positions may correspond to a control node. The control node may relate to a time point at which the multiple components reach the set of positions, respectively. In some embodiments, two sequential control nodes may define a segment. The positions may be predetermined according to, for example, plan data. The plan data may relate to a radiotherapy treatment plan, a scanning imaging plan, or the like, or any combination thereof. The system herein may be a medical system, for example, the radiotherapy (RT) system 100, a computed tomography (CT) system, an ultrasonography system, an X-ray photography system, or the like. Taking the radiotherapy system 100 as an example, the multiple components may include the gantry 113, one or more leaves of a multi-leaf collimator (MLC), the table 116, or the like, or any combination thereof. In some embodiments, the real-time position of a component may be determined or measured by a sensor connected to or communicating with the acquisition module 410.

In 504, motion parameters of the multiple components may be determined based on the position information. The motion parameters of the multiple components may be determined by, for example, the processing module 420. In some embodiments, the motion parameters of a component in a segment may refer to parameters with which the component traverse the segment. The motion parameters may include one or more of an acceleration duration, a cruise duration, a deceleration duration, a cruise velocity, an acceleration, etc. In some embodiments, the processing module 420 may determine motion parameters of each component to traverse a segment based on the position information. In some embodiments, the motion parameters may enable the multiple components to motion in a coordinated manner. More particularly, the motion parameters may enable the multiple components to reach predetermined positions defined by control nodes of the plan data at a same (or roughly the same) time point.

In 506, control instructions for controlling the multiple components may be generated based on the motion parameters. In some embodiments, the control instructions may be generated by the control module 430. In some embodiments, the control instructions may include instructions for controlling velocities and/or real-time positions of the multiple components. The instructions for controlling velocities and/or the positions of the multiple components may be transmitted to a velocity loop and/or a position loop. The position loop may control real-time positions of a component at a plurality of control nodes based on a trajectory curve of the component. In some embodiments, the trajectory curve may be determined based on the motion parameters. The velocity loop may control velocities of a component at or between a plurality of control nodes based on a velocity curve of the component. In some embodiments, the velocity curve may be determined based on the motion parameters.

It should be noted that the above description is merely provided for the purposes of illustration, and not intended to limit the scope of the present disclosure. For persons having ordinary skills in the art, multiple variations or modifications may be made under the teachings of the present disclosure. For example, the process 500 may further include an operation for determining a plurality of optimized durations for the multiple components to traverse a plurality of segments. The motion parameters of the multiple components may be determined based on optimized durations. However, those variations and modifications do not depart from the scope of the present disclosure.

Figure 6:
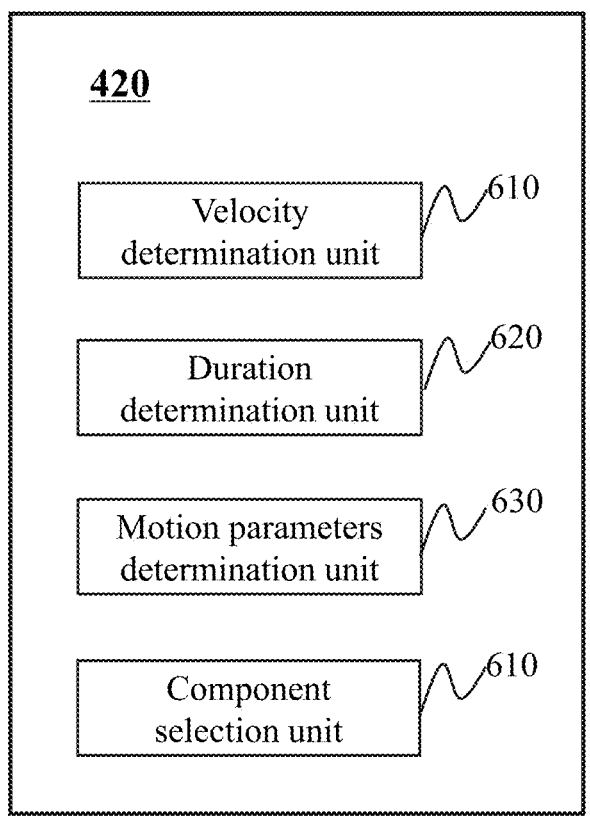
FIG. 6 is a block diagram illustrating an exemplary processing module according to some embodiments of the present disclosure.

FIG. 6 is a block diagram illustrating an exemplary processing module 420 according to some embodiments of the present disclosure. The processing module 420 may include a velocity determination unit 610, a duration determination unit 620, a motion parameters determination unit 630, and a component selection unit 640.

The velocity determination unit 610 may determine a velocity of a component at a control node. The velocity determination unit 610 may obtain positions of one or more control nodes associated with the control node (e.g., plan data), and determine the velocity of the component at the control node based on the positions. In some embodiments, the velocity determination unit 610 may determine whether a velocity of a component at a control node is zero or non-zero. In some embodiments, the velocity determination unit 610 may determine the value of the velocity at the control node. In some embodiments, the velocity determination unit 610 may transmit the velocity of the component to the duration determination unit 620 and/or the motion parameter determination unit 630 for further processing, or transmit to any storage device disclosed in the present disclosure (e.g., the storage module 440, the storage 150) for storage.

The duration determination unit 620 may determine a duration for a component to traverse a segment. In some embodiments, the duration determination unit 620 may obtain velocities of a component at two sequential control nodes of a segment, and determine a velocity mode of the component in the segment based on the velocities at the two sequential control nodes. The velocity mode may refer to a characterization of a velocity curve of a component in a segment. For example, one or more stages (e.g., an acceleration stage, a deceleration stage, a cruise stage, etc.) of a velocity curve may be characterized in the velocity mode. In some embodiments, the duration determination unit 620 may determine a minimum duration for the component to traverse the segment based on the velocity mode and a set of constraints. The set of constraints may relate to the velocity, the acceleration, the jerk, the displacement, and/or mechanical structure of the component in the segment.

In some embodiments, the duration determination unit 620 may further determine an optimized duration corresponding to a segment based on minimum durations for the multiple components to traverse the segment. In some embodiments, duration determination unit 620 may determine the optimized duration corresponding to the segment in a plurality of iterations. In some embodiments, the duration determination unit 620 may transmit the optimized duration corresponding to the segment to the motion parameter determination unit 630 to determine motion parameters of the component in the segment and/or to any storage device disclosed in the present disclosure (e.g., the storage module 440, the storage 150) for storage.

The motion parameter determination unit 630 may determine motion parameters of a component in a segment. In some embodiments, the motion parameter determination unit 630 may obtain a duration (e.g., the optimized duration) corresponding to a segment from the duration determination unit 620, and determine motion parameters of a component in the segment based on the duration. The motion parameters may include one or more of, for example, an acceleration duration, a cruise duration, a deceleration duration, a cruise velocity, an acceleration, etc. For instance, a motion parameter determination unit 630 may use a Double S velocity mode to determine motion parameters of a component in a segment. The motion parameters may be transmitted to the control module 430 for controlling the motions of the multiple components of the radiotherapy device 110 and/or to any storage device disclosed in the present disclosure (e.g., the storage module 440, the storage 150) for storage.

The component selection unit 640 may select one or more components from the multiple components. The component selection unit 640 may select the one or more components before the duration determination unit 620 determines the optimized duration corresponding to each segment. The optimized duration may be determined in a plurality of iterations based on the one or more selected components, rather than all of the multiple components. Merely for illustration purposes, the one or more selected components may include a first component with a larger minimum duration compared to other components, a leaf of the MLC with a larger displacement compared to other leaves moving during a segment according to an acceleration-cruise-deceleration mode, a leaf of the MLC with a larger displacement compared to other leaves moving during a segment according to an acceleration-cruise mode or a cruise-deceleration mode, and/or a leaf of the MLC with a larger displacement compared to other leaves moving during a segment according to a cruise mode.

It should be noted that the above description of the processing module is merely provided for the purposes of illustration, and not intended to limit the scope of the present disclosure. For persons having ordinary skills in the art, multiple variations or modifications may be made under the teachings of the present disclosure. For example, one or more units in the processing module 420 may include an independent storage block (not shown). As another example, any two or more units may be combined as an independent unit used to implement more than one functions. As a further example, any one of the units may be divided into two or more sub-units. However, those variations and modifications do not depart from the scope of the present disclosure.

Figure 7:
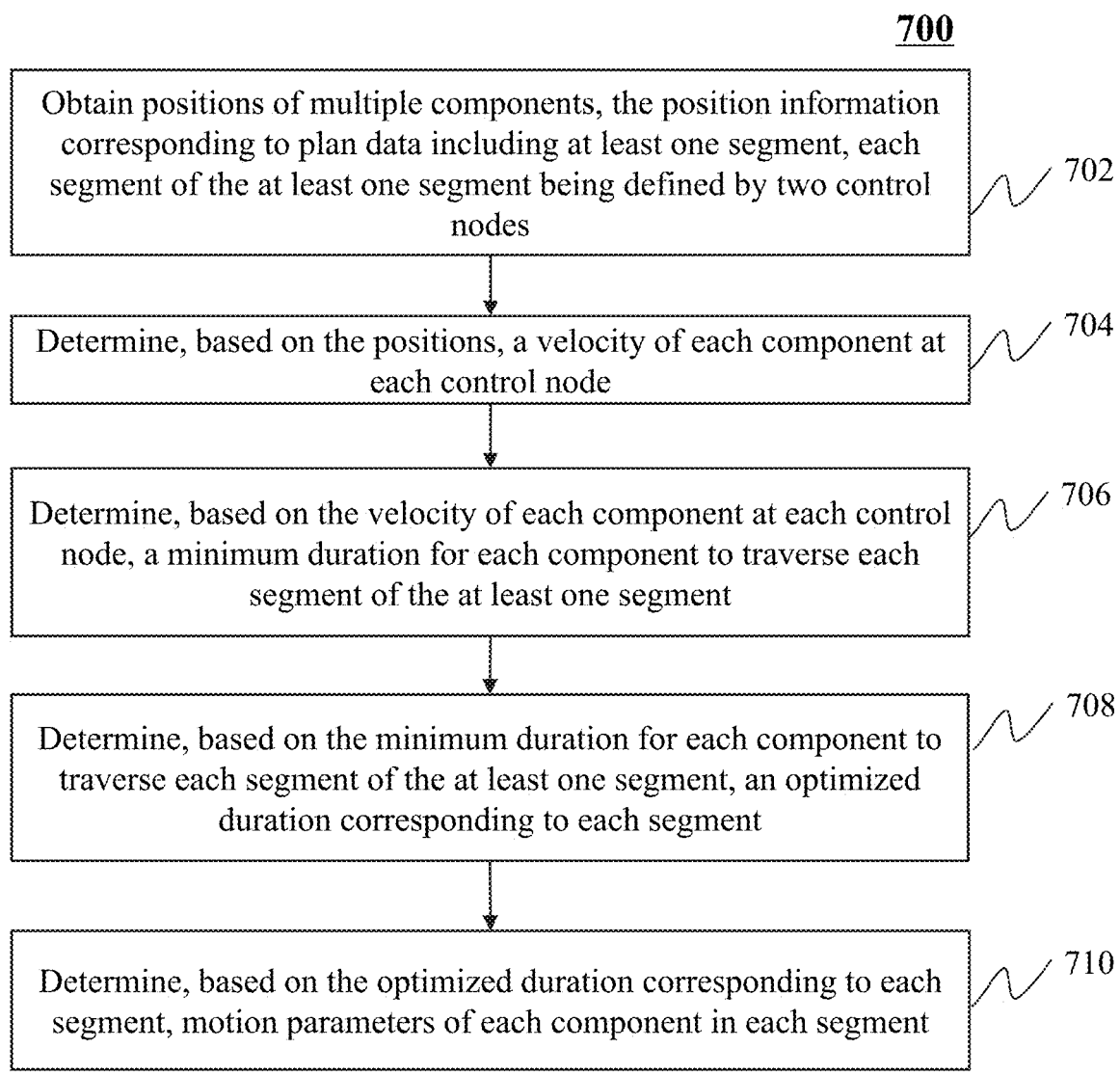
FIG. 7 is a flowchart illustrating an exemplary process for determining motion parameters of multiple components according to some embodiments of the present disclosure.

FIG. 7 is a flowchart illustrating an exemplary process for determining motion parameters of multiple components according to some embodiments of the present disclosure. Process 700 and the other processes described herein may be performed using any suitable combination of hardware, software or manual means. Software embodying these processes may be stored by any non-transitory tangible medium, including a fixed disk, a floppy disk, a CD, a DVD, a Flash drive, or a magnetic tape.

In 702, positions of multiple components may be obtained. The position information may be obtained by, for example, the acquisition module 410. In some embodiments, the operations for obtaining position information of the multiple components in 702 may be the same as or similar to those in 502 of the process 500, the description of which is not repeated here.

In 704, a velocity of each component at each control node may be determined based on the position information. In some embodiments, the velocity of each component at each control node may be determined by, for example, the velocity determination unit 610. In some embodiments, a determination may be made as to whether the velocity of each component at each control node is zero.

For illustration purposes, an example of determining the velocity of a component at a current control node may be set forth below. In some embodiments, the velocity at the current control node may be determined based on one or more displacements corresponding to one or more control nodes preceding or subsequent to the current control node. In some embodiments, the one or more control nodes may include a prior control node and a subsequent control node. As used herein, the prior control node may refer to a control node before the current control node as well as being next to the current control node. The subsequent control node may refer to a control node after the current control node as well as being next to the current control node. Merely for illustration purposes, taking a current control node $CP_i$ as an example, a control node $CP_{i-1}$ may be defined as the prior control node relative to the current control node $CP_i$, and a control node $CP_{i+1}$ may be defined as the subsequent control node relative to the current control node $CP_i$. In some embodiments, the one or more displacements may be determined based on the position information in the plan data. For example, for a gantry with a rotation angle of 5 degrees at the prior control node, 10 degrees at the current control node, and 15 degrees at the subsequent control node, the one or more displacements corresponding to the prior control node, the current control node, and the subsequent control node may be 5 degrees, 10 degrees, and 15 degrees, respectively. In some embodiments, a displacement may refer to the displacement between a control node and a reference control node. Merely by way of example, the reference control node may be a starting control node of the plan data, an ending control node of the plan data, a prior control node of a current control node, a subsequent control node of a current control node, or the like. As used herein, the starting control node may refer to a first control node of the control nodes of the plan data in terms of time. The ending control node may refer to a last control node of the control nodes of the plan data in terms of time. For example, for plan data including M+1 control nodes (e.g., CP=[$CP_0$, $CP_1$, $CP_2$, $CP_3$, . . . , $CP_m$]), $CP_0$ may be the starting control node, and $CP_m$ may be the ending control node. In some embodiments, the one or more displacements may be displacements between the one or more control nodes and their respective prior control nodes.

In some embodiments, a determination may be made as to whether the one or more displacements conform to a monotonic change with time. If the one or more displacements conform to a monotonic change with time, the velocity at the control node may be non-zero. If the one or more displacements fail to conform to a monotonic change with time, the velocity at the control node may be designated as zero.

Taking a control node $CP_i$ as an example, the velocity determination unit 610 may determine displacements $\varepsilon(CP_{i-1})$, $\varepsilon(CP_i)$, and $\varepsilon(CP_{i+1})$ corresponding to the control nodes $CP_{i-1}$, $CP_i$, and $CP_{i+1}$, respectively. The velocity of the control node $CP_i$ may be determined based on the displacements $\varepsilon(CP_{i-1})$, $\varepsilon(CP_i)$, and $\varepsilon(CP_{i+1})$. The displacements $\varepsilon(CP_{i-1})$, $\varepsilon(CP_i)$, and $\varepsilon(CP_{i+1})$ may represent displacements between the control nodes $\varepsilon(CP_{i-1})$, $\varepsilon(CP_i)$, and $\varepsilon(CP_{i+1})$ and a reference control node $CP_0$, respectively. If the displacements $\varepsilon(CP_{i-1})$, $\varepsilon(CP_i)$, and $\varepsilon(CP_{i+1})$ conform to a monotonic change with time (e.g., $\varepsilon(CP_{i-1}) \geq \varepsilon(CP_i) \geq \varepsilon(CP_{i+1})$, or $\varepsilon(CP_{i-1}) \leq \varepsilon(CP_i) \leq \varepsilon(CP_{i+1})$), the velocity of the control node $\varepsilon(CP_i)$ may be non-zero. If the displacements $\varepsilon(CP_{i-1})$, $\varepsilon(CP_i)$, and $\varepsilon(CP_{i+1})$ fail to conform to a monotonic change with time (e.g., $\varepsilon(CP_{i-1}) > \varepsilon(CP_i)$, $\varepsilon(CP_i) < \varepsilon(CP_{i+1})$, or $\varepsilon(CP_{i-1}) < \varepsilon(CP_i)$, $\varepsilon(CP_i) > \varepsilon(CP_{i+1})$), the velocity of the control node $\varepsilon(CP_i)$ may be designated as zero.

In 706, a minimum duration for each component to traverse each segment of the at least one segment may be determined based on the velocity of each component at each control node. In some embodiments, the minimum duration may be determined by the duration determination unit 620. In some embodiments, a velocity mode of each component may be determined for each segment, and the minimum duration for each component to traverse each segment may be determined based on the velocity mode. In some embodiments, a velocity mode may include one or more motion mode (e.g., acceleration, cruise, or deceleration). Exemplary velocity modes may include an acceleration-cruise-deceleration mode, a cruise mode, an acceleration-deceleration mode, an acceleration-cruise mode, a cruise-deceleration mode, a deceleration-cruise-acceleration mode, a deceleration-acceleration mode, or the like, or any combination thereof. The acceleration-cruise-deceleration mode may include an acceleration stage, a cruise stage, and a deceleration stage. The acceleration-cruise mode may include an acceleration stage and a cruise stage. The cruise-deceleration mode may include a cruise stage and a deceleration stage. The cruise mode may include a cruise stage. The acceleration-deceleration mode may include an acceleration stage and a deceleration stage. In some embodiments, a component may traverse different segments with different velocity modes.

In some embodiments, the velocity mode with which a component may traverse a segment defined by two control nodes may be determined based on the velocities of the component at the two control nodes. Merely by way of example, for a segment $S_j$ defined by control nodes $CP_{j-1}$ and $CP_j$, if velocities of a component at both of the two control nodes $CP_{j-1}$ and $CP_j$ are non-zero, the component may traverse the segment $S_j$ with a cruise mode, an acceleration-cruise-deceleration mode, an acceleration-deceleration mode, a deceleration-cruise-acceleration mode, or a deceleration-acceleration mode. As another example, if velocities of a component at both of the two control nodes $CP_{j-1}$ and $CP_j$ are zero, the component may traverse the segment $S_j$ with an acceleration-cruise-deceleration mode or an acceleration-deceleration mode.

In some embodiments, the minimum duration for a component to traverse a segment may be determined based on the velocity mode of the component in the segment. In some embodiments, a duration corresponding to each motion status in the velocity mode may be determined. The minimum duration for the component to traverse the segment may be obtained by determining a sum of the duration corresponding to each motion mode in the velocity mode. Details regarding the determination of the minimum duration based on the velocity mode may be found elsewhere in the present disclosure. See, for example, FIG. 12 and the descriptions thereof.

In some embodiments, a maximum duration for a component to traverse a segment may be determined according to the acceleration-cruise-deceleration mode. For example, if the velocities of the multiple components are zero at the two control nodes of the segments (i.e., each component has an entry velocity $V_{enter}=0$ and an exit velocity $V_{exit}=0$), a duration for a component to traverse a segment determined according to the acceleration-cruise-deceleration mode may be designated as the maximum duration for the component to traverse the segment.

In 708, an optimized duration corresponding to each segment may be determined based on the minimum duration for each component to traverse each segment of the at least one segment. In some embodiments, the optimized duration corresponding to a segment may refer to a minimized duration at the end of which all of the multiple components arrive at positions defined by an ending control node of the segment. For example, for a segment $S_j$ defined by control nodes $CP_{j-1}$ and $CP_j$, if the optimized duration is 10 seconds, all of the multiple components have arrived at positions defined by the control node $CP_j$ after 10 seconds.

In some embodiments, a candidate minimum duration corresponding to a segment may be determined based on the minimum duration for each component to traverse the segment. 第 80 段 The candidate minimum duration may be designated as a lower limit when the optimized duration corresponding to the segment may be determined. The optimized duration corresponding to the segment may be the same as or larger than the candidate minimum duration.

In some embodiments, the optimized duration may be determined in one or more iterations. During each of the one or more iterations, the candidate minimum duration may be updated (e.g., increased by an increment in each iteration). In some embodiments, when a termination condition is satisfied, the iteration may terminate, and the candidate minimum duration may be designated as the optimized duration. Details regarding the determination of the optimized duration corresponding to a segment may be found elsewhere in the present disclosure. See, for example, FIG. 8 and the descriptions thereof. In some embodiments, a candidate maximum duration corresponding to a segment may be determined based on the maximum duration for each component to traverse the segment. For example, a maximum duration for a component to traverse a segment that is larger than those for the other components to traverse the segment (i.e. the largest maximum duration) may be designated as the candidate maximum duration for the segment. The candidate maximum duration may be designated as an upper limit of the optimized duration corresponding to the segment. The optimized duration may be determined from a range of values from the candidate minimum duration to the candidate maximum duration. In some embodiments, the maximum duration and the candidate maximum duration may be omitted when the optimized duration is determined.

In 710, motion parameters of each component in each segment may be determined based on the optimized duration corresponding to each segment. In some embodiments, the motion parameters may be used to control synchronous motions of multiple components from a starting control node to an ending control node of each segment. The motion parameters may include, for example, an acceleration duration, a cruise duration, a deceleration duration, a cruise velocity, an acceleration, etc. In some embodiments, the motion parameters of a component for a segment may be determined based on the optimized duration for the segment. For example, the velocity of each component at each control node may be determined after the optimized durations are determined for the at least one segments. In some embodiments, the velocity of a component at a control node may be determined according to formula (1):

$$V_{CP(j)} = \begin{cases} 0 & \text{if non-monotonic} \\ \dfrac{2}{1/V_{Av(j)} + 1/V_{Av(j+1)}} & \text{if monotonic} \end{cases} \quad (1)$$

where $CP_j$ denotes the control node, $V_{CP(j)}$ denotes the velocity of a component at the control node, $V_{Av(j)}$ denotes an average velocity of the component in a segment $S_j$ defined by control nodes $CP_{j-1}$ and $CP_j$, and $V_{Av(j+1)}$ denotes an average velocity of the component in a segment $S_{j+1}$ defined by control nodes $CP_j$ and $CP_{j+1}$. The average velocity $V_{Av(j)}$ may be determined according to formula (2):

$$V_{Av(j)} = (\varepsilon(CP_j) - \varepsilon(CP_{j-1}))/h_j, \quad (2)$$

where $\varepsilon(CP_j)$ and $\varepsilon(CP_{j-1})$ denotes the displacements corresponding to the control nodes $CP_j$ and $CP_{j-1}$, respectively, and $h_j$ denotes a duration for the component to traverse the segment $S_j$ (e.g., an optimized duration determined in 708). In some embodiments, the velocity of each component at each control node may be used to determine the motion parameters of each component in each segment based on a velocity mode of a component in each segment and other techniques (e.g., a Double S model).

In some embodiments, control instructions may be generated based on the motion parameters. The synchronous motions of the multiple components may be controlled according to the control instructions. In some embodiments, the control instructions may include, for example, velocity curves of the multiple components, trajectory curves of the multiple components, or the like. In some embodiments, the velocity curve of a component may include a plurality of velocities and corresponding time points at which the component reaches the plurality of velocities. In some embodiments, the trajectory curve of a component may include a plurality of positions and corresponding time points at which the component arrives at the plurality of positions.

In some embodiments, the motion parameters of a segment may depend on the segment itself and also other segments. For instance, the position, exit velocity, etc., of a component at the ending control node of a segment is the position, entry velocity, etc., of the component at the beginning of the subsequent segment. The determination of the motion parameters of a segment (e.g., an optimized duration of the segment) may be based on parameters of the segment itself, e.g., the candidate minimum duration of the segment, and also parameters of other segments (e.g., the candidate minimum durations of other segments).

It should be noted that the above description is merely provided for the purposes of illustration, and not intended to limit the scope of the present disclosure. For persons having ordinary skills in the art, multiple variations or modifications may be made under the teachings of the present disclosure. For example, the process 700 may further include operations for generating control instructions for controlling motions of the multiple components in the at least one segments, and transmitting the control instructions to the control module 430. However, those variations and modifications do not depart from the scope of the present disclosure.

Figure 8:
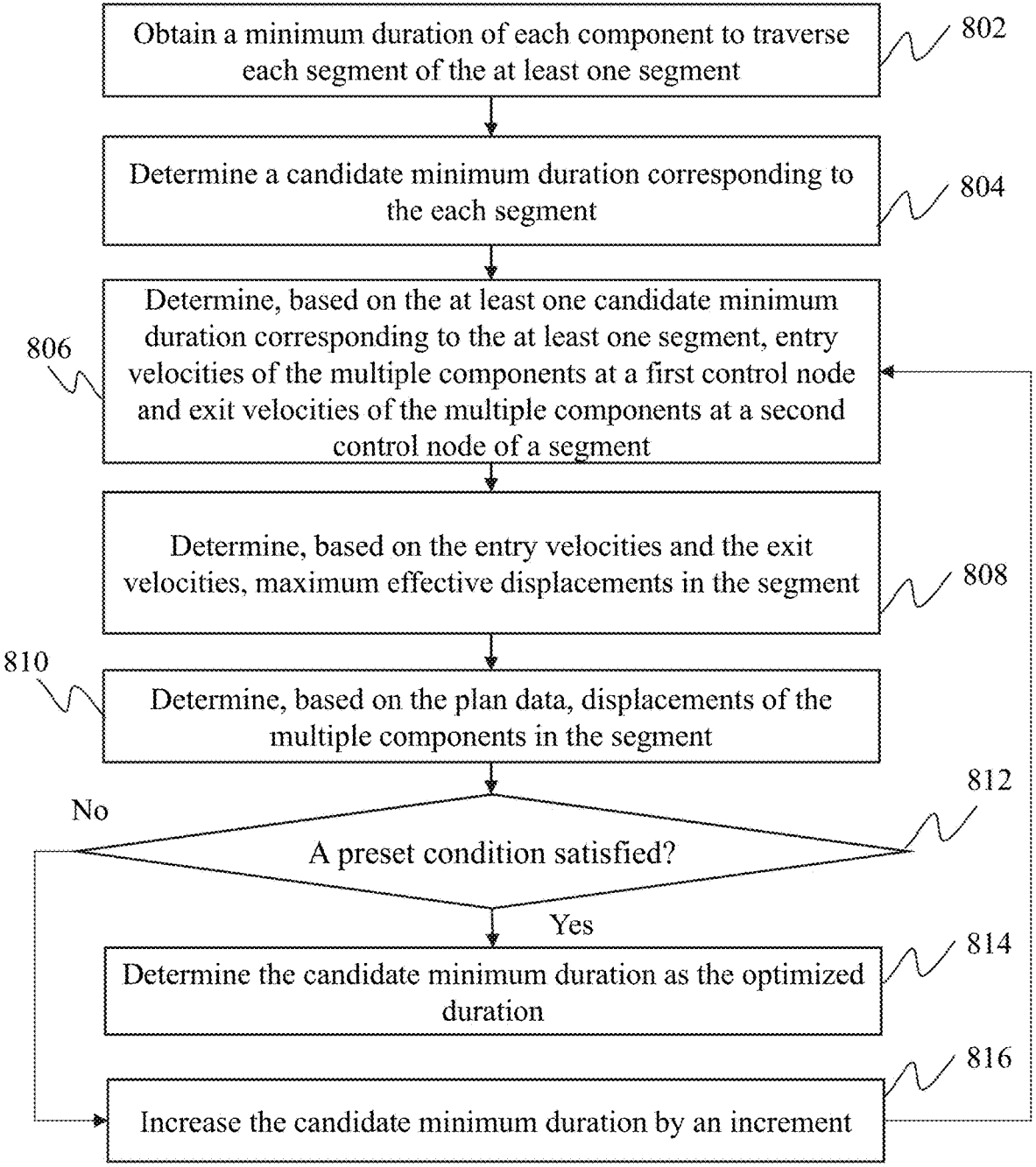
FIG. 8 is a flowchart illustrating an exemplary process for determining an optimized duration according to some embodiments of the present disclosure.

FIG. 8 is a flowchart illustrating an exemplary process 800 for determining an optimized duration for a segment according to some embodiments of the present disclosure. Process 800 and the other processes described herein may be performed using any suitable combination of hardware, software or manual means. Software embodying these processes may be stored by any non-transitory tangible medium, including a fixed disk, a floppy disk, a CD, a DVD, a Flash drive, or a magnetic tape.

In 802, a minimum duration for each component to traverse each segment of the at least one segment may be obtained. In some embodiments, the minimum duration for each component to traverse each segment may be determined by, for example, performing operations in 706, the description of which is not repeated here.

In 804, a candidate minimum duration corresponding to each segment may be determined. For plan data including m segments, m candidate minimum durations may be determined. A candidate minimum duration corresponding to a segment may be the lower limit of the optimized duration corresponding to the segment may be determined.

In some embodiments, the candidate minimum duration corresponding to a segment may be determined based on minimum durations of the multiple components corresponding to the segment. In some embodiments, a minimum duration for a component to traverse a segment that is larger than the minimum durations of other components may be designated as the candidate minimum duration (also referred to as "initial candidate minimum duration") for the segment. The candidate minimum duration corresponding to the segment may be a lower limit of the range within which the optimized duration corresponding to the segment may be determined. For example, if the minimum duration for the gantry to traverse a segment is larger than the minimum durations of other components (e.g., the leaves of the MLC, the collimator, and the table), the minimum duration for the gantry to traverse the segment may be designated as the candidate minimum duration for the segment.

In some embodiments, at least one candidate minimum duration corresponding to the at least one segment may be determined based on the minimum duration for each component to traverse each segment of the at least one segment. In some embodiments, the at least one candidate minimum duration may be in the form of a matrix or a vector. For example, the at least one candidate minimum duration may be in a row matrix expressed in formula (3):

$$H=[h_1,h_2,h_3,\ldots,h_m], \quad (3)$$

where m denotes the number of the segments, H denotes the row matrix, and $h_1$ through $h_m$ denotes the candidate minimum durations corresponding to each of the m segments, respectively. As another example, the at least one candidate minimum duration may be in the form of a one-dimension vector.

In 806, entry velocities of the multiple components at a starting control node and exit velocities of the multiple components at an ending control node of a segment may be determined based on the at least one candidate minimum duration corresponding to the at least one segment. For a segment defined by two control nodes, a velocity at the starting control node may be referred to as an entry velocity, and a velocity at the ending control node may be referred to as an exit velocity. The starting control node of a segment may refer to the control node at the beginning of the segment. The ending control node of a segment refer to the control node at the end of the segment. Merely for illustration purposes, for a segment $S_j$ defined by control node $CP_{j-1}$ and $CP_j$, the control node $CP_{j-1}$ may be referred as to the starting control node of the segment $S_j$ and the control node $CP_j$ may be referred as to the ending control node of the segment $S_j$. The entry velocities may refer to the velocities of the multiple components at the starting control node. The exit velocities may refer to the velocities of the multiple components at the ending control node. In some embodiments, the velocities of the multiple components at the starting control node and exit velocities of the multiple components at the ending control node may be determined based on the at least one candidate minimum durations. For example, the entry velocities and the exit velocities may be determined by incorporating the at least one candidate minimum durations into formulae (1) and (2).

In some embodiments, the candidate minimum duration for a segment may be updated in a plurality of iterations to determine an optimized duration for the segment. To improve efficiency, one or more components may be identified from the multiple components such that the plurality of iterations for determining the optimized duration for a segment are performed with respect to the identified one or more components prior to the other components. Merely for illustration purposes, the one or more components may be considered at first in the iterative process (e.g., 806 through 816). If the preset condition is not satisfied with respect to at least one of the identified one or more components, another round of iteration may be performed. A potential candidate minimum duration for the segment may be determined if the preset condition is satisfied with respect to all of the identified one or more components. Then the potential candidate minimum duration for the segment may be tested with respect to other components of the multiple components. If the preset condition is satisfied with respect to all other components, the potential candidate minimum duration for the segment may be designated as the candidate minimum duration for the segment. If the preset condition fails to be satisfied with respect to at least one of the other components, another round of iteration may be performed, starting with the identified one or more components. The one or more components may be determined by, for example, the component selection unit 640. Merely for illustration purposes, four components including a first component, a second component, a third component, and a fourth component may be determined for each segment.

In some embodiments, for a segment, a component with a larger minimum duration compared to other components may be determined as the first component. In some embodiments, the minimum duration for each component to traverse a segment may be determined, for example, by performing 706 of the process 700.

In some embodiments, the MLC may have multiple leaves (e.g., 120 leaves), and each leaf of the MLC may be determined as a component. In some embodiments, various velocity modes may be taken into consideration when the one or more components are determined. Merely for illustration purposes, for two leaves of the MLC with the same displacements in a segment, the minimum durations may be different if the two leaves traverse the segment according to different velocity modes. In some embodiments, for one or more leaves traversing the segment with zero entry velocities and zero exit velocities, a leaf with a larger displacement compared to other leaves of the MLC may be determined as the second component. In some embodiments, for one or more leaves traversing the segment with zero entry velocities and non-zero exit velocities or with non-zero entry velocities and zero exit velocities of zero, a leaf with a larger displacement compared to other leaves of the MLC may be determined as the third component. In some embodiments, for one or more leaves with non-zero entry velocities and non-zero exit velocities, a leaf with a larger displacement compared to other leaves of the MLC may be determined as the fourth component.

In 808, maximum effective displacements of the multiple components in the segment may be determined based on the entry velocities and the exit velocities of the multiple components. In some embodiments, a maximum effective displacement of a component in a segment may be determined based on a maximum effective velocity of the component in the segment. The maximum effective velocity may refer to a peak velocity that the component can reach when traversing a segment in the candidate minimum duration. The maximum effective displacement of a component in a segment may refer to a displacement that the component can reach with the maximum effective velocity in the candidate minimum duration. In some embodiments, minimum effective displacements of the multiple components in the segment may be determined based on the entry velocities and the exit velocities of the multiple components. In some embodiments, a minimum effective displacement of a component in a segment may be determined based on a minimum effective velocity of the component in the segment. The minimum effective velocity of a component in a segment may refer to a minimum velocity that the component can reach when traversing the segment in the candidate minimum duration. The minimum effective displacement may refer to a displacement that the component can reach with the minimum effective velocity in the candidate minimum duration. In some embodiments, the maximum effective velocity and/or the minimum effective velocity of a component in a segment may be determined in a plurality of iterations. Details regarding the determination of the maximum effective displacement, and the minimum effective displacement of a component in a segment may be found elsewhere in the present disclosure. See, for example, FIG. 13 and the descriptions thereof.

In 810, displacements of the multiple components in the segment may be determined based on the plan data. In some embodiments, a displacement of a component in a segment may be determined based on position information in the plan data. In some embodiments, the displacement of a component in a segment may be determined based on the position of the component at the starting control node and the position of the component at the ending control node. For example, if rotation angles of the gantry at two sequential control nodes of a segment are 10 degrees and 15 degrees, respectively, the displacement of the gantry in the segment may be 5 degrees. As another example, if positions of a leaf of the MLC at two sequential control nodes of a segment are −1 centimeter and 1 centimeter, respectively, the displacement of the leaf in the segment may be 2 centimeters.

In 812, a determination may be made as to whether a preset condition is satisfied. If the preset condition is satisfied, the process 800 may proceed to 814 in which the candidate minimum duration may be designated as the optimized duration. If the pre-set condition is not satisfied, the process 800 may proceed to 816 to increase the candidate minimum duration by an increment, and another round of iteration including 806 through 814 may be performed.

In some embodiments, the preset condition may be that the displacement of each component of the multiple components is smaller than the maximum effective displacement. Merely for illustration purposes, for a segment, if the displacement of each component is smaller than the maximum effective displacement, which may indicate that all of the multiple components can traverse the segment within the candidate minimum duration, the preset condition may be deemed satisfied. In some embodiments, the preset condition may be that the displacement of each component of the multiple components is between the maximum effective displacement and the minimum effective displacement of the component. Merely for illustration purposes, for a segment, if the displacement of each component is between the minimum effective displacement and the maximum effective displacement, which may indicate that all of the multiple components can traverse the segment within the candidate minimum duration, the preset condition may be deemed satisfied. In some embodiments, the preset condition may be a predetermined threshold for the candidate minimum duration that when the candidate minimum duration is larger than the predetermined threshold, the iteration may terminate. In some embodiments, the predetermined threshold may be set by a user and/or according to default settings of the radiotherapy system 100. In some embodiments, if the velocities of the multiple components are zero at the two control nodes of the segments (i.e., each component has an entry velocity $V_{enter}=0$ and an exit velocity $V_{exit}=0$), a minimum duration of a component larger than those for other components (i.e. the largest minimum duration) may be designated as the predetermined threshold for the segment.

In 814, the candidate minimum duration may be determined as the optimized duration for the segment. The optimized duration for the segment may be used to determine motion parameters of the multiple components in the segment.

In 816, the candidate minimum duration may be increased by an increment. If the displacement of at least one component is larger than the maximum effective displacement of the at least one component, which indicates that the at least one component may not traverse the entire segment within the candidate minimum duration, the candidate minimum duration may be increased by an increment, and an updated candidate minimum duration may be obtained. The increment may be a value (e.g., 2 seconds, 15 seconds, 1 minute, etc.) set by a user, according to a default setting of the radiotherapy system 100. Merely for illustration purposes, for a segment $S_j$, if the preset condition is not satisfied, an updated candidate minimum duration of the segment $S_j$ may be determined according to formula (4):

$$h_j' = h_j + \Delta h \quad (4)$$

where $\Delta h$ denotes the increment, $h_j'$ denotes the updated candidate minimum duration, and $h_j$ denotes the candidate minimum duration. In some embodiments, a new set of candidate minimum durations corresponding to the at least one segment may be determined. The new set of candidate minimum durations may be used to determine optimized duration corresponding to segment $S_{j-1}$. The segment $S_{j-1}$ may be prior to the segment $S_j$ in terms of time. Merely for illustration purposes, if the candidate minimum duration of the segment $S_j$ is changed (e.g., increased by an increment), the exit velocities, the maximum effective displacements, and the minimum effective displacements of the multiple components in the segment $S_{j-1}$ may change, accordingly. The new set of candidate minimum durations may be expressed in formula (5):

$$h_n = [h_1, h_2, h_3, \ldots, h_j', \ldots, h_m], \quad (5)$$

where n denotes the iteration count, i.e. which round of the iteration is currently performed.

It should be noted that the above description is merely provided for the purposes of illustration, and not intended to limit the scope of the present disclosure. For persons having ordinary skills in the art, multiple variations or modifications may be made under the teachings of the present disclosure. For example, for two sequential segments, the iterative operations in 806 through 816 may be repeated to determine a second optimized duration corresponding to a second segment of the at least one segment in a second plurality of iterations after the determination of a first optimized duration corresponding to a first segment of the at least one segment in a first plurality of iterations, in which the first segment may precede the second segment. Merely for illustration purposes, for plan data including m segments (e.g., $S=[S_1, S_2, S_3, \ldots, S_j, S_{j+1}, \ldots S_m,]$), the determination of the optimized duration for segments $S_{j+1}$ may be initiated after the determination of the optimized duration for segments $S_j$ is finished. As another example, operations in 806 through 812 may be substituted with other alternative operations for evaluating a candidate minimum duration (e.g., determining whether a candidate minimum duration can be an optimized duration for a segment). However, those variations and modifications do not depart from the scope of the present disclosure.

FIG. 9 illustrates exemplary plan data according to some embodiments of the present disclosure. The plan data may relate to a plan (e.g., a radiation treatment plan for providing a sequence of radiation beams), which may include a plurality of sets of positions of multiple components (e.g., a gantry, one or more leaves of a multi-leaf collimator (MLC), etc.). In some embodiments, the plan data may include a plurality of discrete control nodes. Each control node of the control nodes may include positions of the multiple components at a time point, as well as the cumulative radiation dose delivered until the time point. The transition between two sequential control nodes may be defined as a segment. In some embodiments, the plan data may include at least one segment. As shown in FIG. 9, the plan data may include m+1 control nodes $CP_0$ through $CP_m$. Each control node of the control nodes $CP_0$ through $CP_m$ includes the position of a gantry (e.g., measured in the angle of the gantry), the position of each leaf of a multi-leaf collimator (MLC), and the cumulative radiation dose (measured in a radiation sensor) delivered until a time point corresponding to the control node. In some embodiments, the radiation dose to be delivered may also be determined as a component. More descriptions regarding the plan data or the positions of the multiple components may be found in, e.g., U.S. Pat. No. 8,503,608 B2, the contents of which are incorporated herein by reference.

Figure 10:
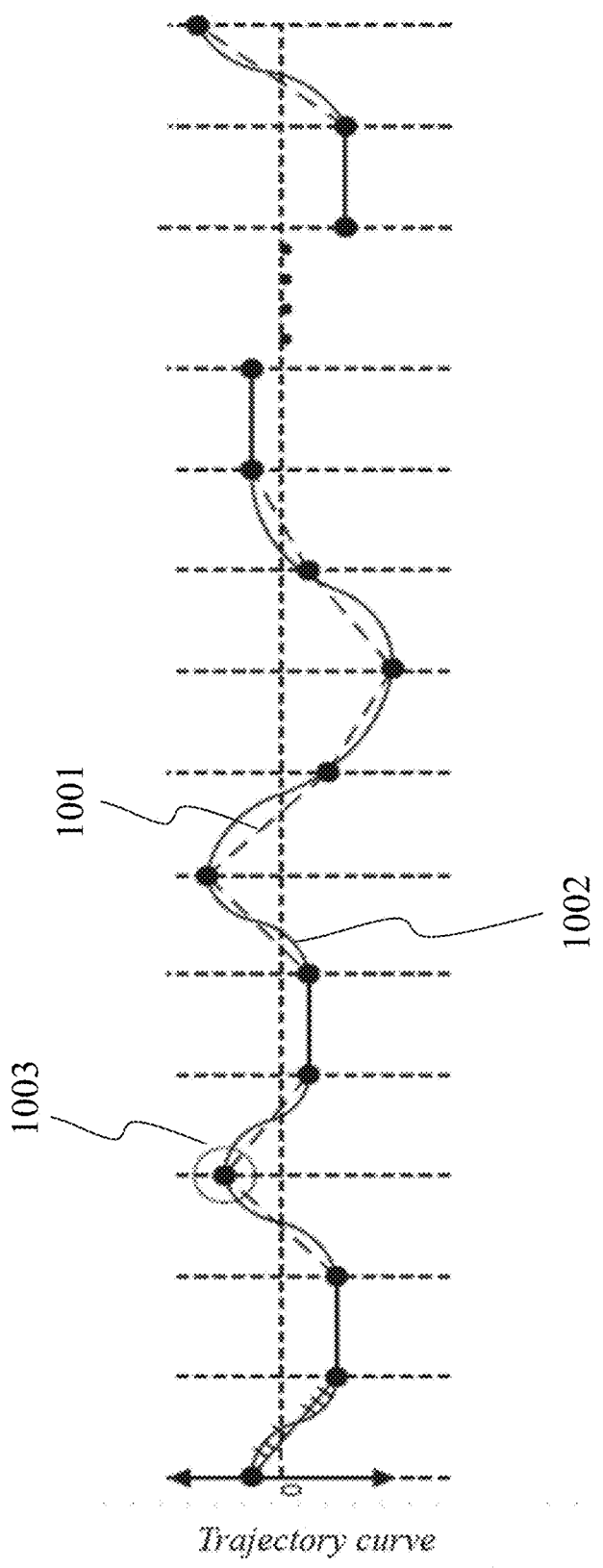
FIG. 10 illustrates an exemplary trajectory curve of a component according to some embodiments of the present disclosure.

FIG. 10 illustrates an exemplary trajectory curve of a component according to some embodiments of the present disclosure. The horizontal axis represents the time or segment time, and the vertical axis represents the position of a component. The trajectory curve 1001, represented by a dashed line, may be generated by a trajectory generation framework including a plurality of features. The features may include, for example, a velocity mode, a minimum duration, as well as a set of constraints. The set of constraints include, for example, jerk, acceleration, velocity, or the like. In some embodiments, the trajectory curve 1001 of the component may be generated based on motion parameters determined according to 710 in the process 700. As illustrated in FIG. 10, the trajectory curve 1001 may fluctuate around the horizontal axis, which indicates that the component may move in a reciprocating trajectory around an origin. In some embodiments, the component may be a leaf of the MLC. The trajectory curve 1001 may include a plurality of via points, for example, the via point 1003. A via point may represent a position that the component may arrive at a time point. In some embodiments, each via point may correspond to a control node. A time interval between two sequential control nodes may represent a duration in which the component may traverse a segment defined by the two sequential control nodes.

In some embodiments, the component may traverse a segment in an actual trajectory 1002 represented by the solid line illustrated in FIG. 10. In some embodiments, there may be a deviation between the trajectory curve 1001 and the actual trajectory 1002. A larger number of control nodes may lead to a smaller deviation. In some embodiments, the number of the control nodes may be optimized to reduce the deviation as well as to improve efficiency in determining the optimized duration and motion parameters of the multiple components in the process 700.

Figure 11:
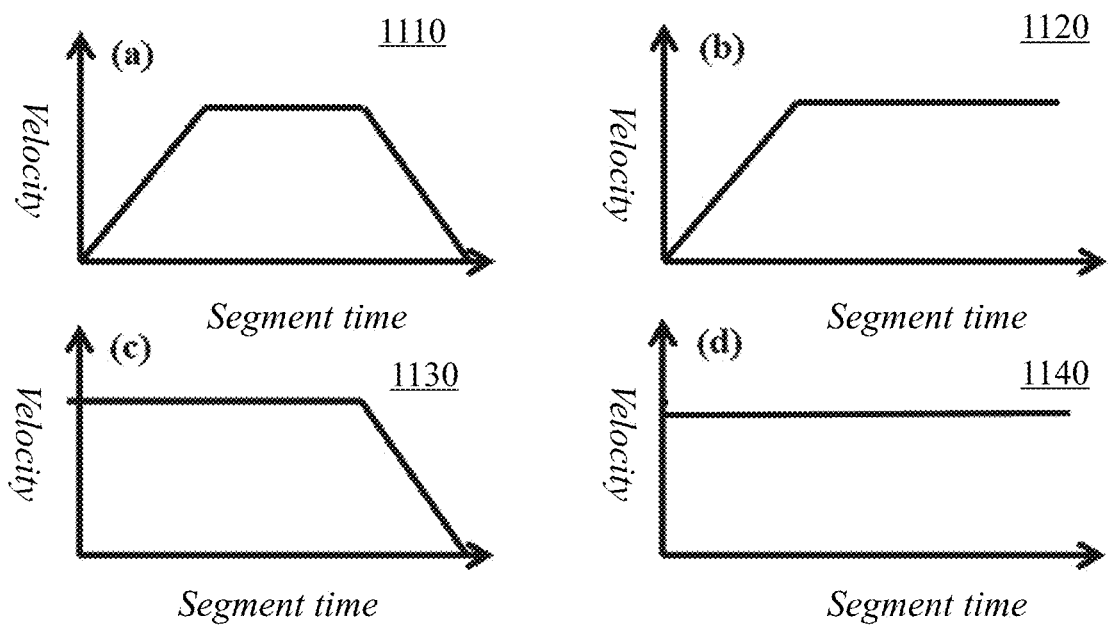
FIG. 11 illustrates exemplary velocity modes of a component according to some embodiments of the present disclosure.

FIG. 11 illustrates exemplary velocity modes of a component according to some embodiments of the present disclosure. In (a) through (d) of FIG. 11, the horizontal axis represents the time or segment time, and the vertical axis represents the velocity of a component. In some embodiments, the velocity modes may include, for example, an acceleration-cruise-deceleration mode 1110, an acceleration-cruise mode 1120, a cruise-deceleration mode 1130, a cruise mode 1140, or the like. In some embodiments, the velocity mode of a component in a segment may be determined based on an entry velocity (i.e., the velocity at a starting control node of the segment) and an exit velocity (i.e., the velocity at an ending control node of the segment) of the component for the segment.

In some embodiments, if both the entry velocity and the exit velocity are zero, the velocity mode of the component may conform to the acceleration-cruise-deceleration mode 1110 in the segment. According to the acceleration-cruise-deceleration mode 1110, the component may accelerate from the entry velocity to a cruise velocity in an entry settling time, cruise at the cruise velocity in a cruise time, then decelerate from the cruise velocity to the exit velocity in an exit settling time. As used herein, the entry settling time may refer to a duration in which the velocity of the component change from an entry velocity to a cruise velocity. The exit settling time may refer to a duration in which the velocity of the component change from a cruise velocity to an exit velocity. A minimum duration for the component to traverse the segment may be determined according to formula (6):

$$\begin{cases} V_{entry} = 0, V_{exit} = 0, |V(t)| \le V_{max}, |A(t) = \dot{V}(t)| \le A_{max} \\ \int_{T_{entry}}^{T_{entry}+T_{en}} V(t)dt + V_{cruise} \cdot T_{curise} + \int_{T_{exit}-T_{ex}}^{T_{exit}} V(t)dt = D, \\ h_{min} = T_{en} + T_{curise} + T_{ex} \end{cases} \quad (6)$$

where V(t) denotes a velocity function of the component across the segment, $V_{entry}$ denotes the entry velocity of the component, $V_{cruise}$ denotes the cruise time, $V_{exit}$ denotes the exit velocity of the component, $V_{max}$ denotes an upper limit of the velocity of the component, t denotes time, $\dot{V}(t)$ denotes the derivative of the velocity function V (t), A(t) denotes the acceleration function of the component across the segment, $A_{max}$ denotes an upper limit of the acceleration of the component, $T_{en}$ denotes the entry settling time, $T_{curise}$ denotes the cruise time, $T_{ex}$ denotes the exit settling time, $T_{entry}$ denotes the time point when the component enters the segment, $T_{exit}$ denotes the time point when the component leaves the segment, D denotes the displacement of the component in the segment, and $h_{min}$ denotes the minimum duration. The minimum duration for the component to traverse the segment may be a sum of the acceleration time $T_{en}$, the cruise time $T_{curise}$, and the exit settling time $T_{ex}$. In some embodiments, constraints related to the jerk may also be considered. For example, the constraints related to the jerk may be expressed in formula (7):

$$|J(t)=\dddot{V}(t)| \le J_{max} \quad (7)$$

where $\ddot{V}$ (t) denotes the second-order derivative of the velocity function V(t), J(t) denotes the jerk, and $J_{max}$ denotes an upper limit of the jerk of the component.

In some embodiments, if the entry velocity is zero, and the exit velocity is non-zone, the velocity mode of the component may conform to the acceleration-cruise mode 1120 in the segment. According to the acceleration-cruise mode 1120, the component may accelerate from the entry velocity to a cruise velocity in an entry settling time, then cruise at the cruise velocity in a cruise time. If the entry velocity is non-zone and the exit velocity is zero, the velocity mode of the component may conform to the cruise-deceleration mode 1130 in the segment. According to the cruise-deceleration mode 1130, the component may cruise at the cruise velocity in a cruise time, then decelerate from the cruise velocity to the exit velocity in an exit settling time. Taking the acceleration-cruise mode 1120 as an example, the minimum duration for the component to traverse the segment may be determined according to formula (8):

$$\begin{cases} V_{entry} = 0, |V(t)| \le V_{max}, |A(t) = \dot{V}(t)| \le A_{max} \\ \int_{T_{entry}}^{T_{entry}+T_{en}} V(t)dt + V_{cruise} \cdot T_{curise} = D, \\ h_{min} = T_{en} + T_{curise} \end{cases} \quad (8)$$

The minimum duration for the component to traverse the segment may include the entry settling time $T_{en}$ and the cruise time $T_{curise}$. In some embodiments, the constraints (e.g., as expressed in formula (7)) related to the jerk may also be considered.

In some embodiments, if both the entry velocity and the exit velocity are non-zero, the velocity mode of the component may conform to cruise mode 1140. According to the cruise mode 1140, the component may traverse the segment at the cruise velocity in a cruise time. The minimum duration for the component to traverse the segment may be determined according to formula (9):

$$h_{min}=D/V_{max}, \quad (9)$$

Figure 12:
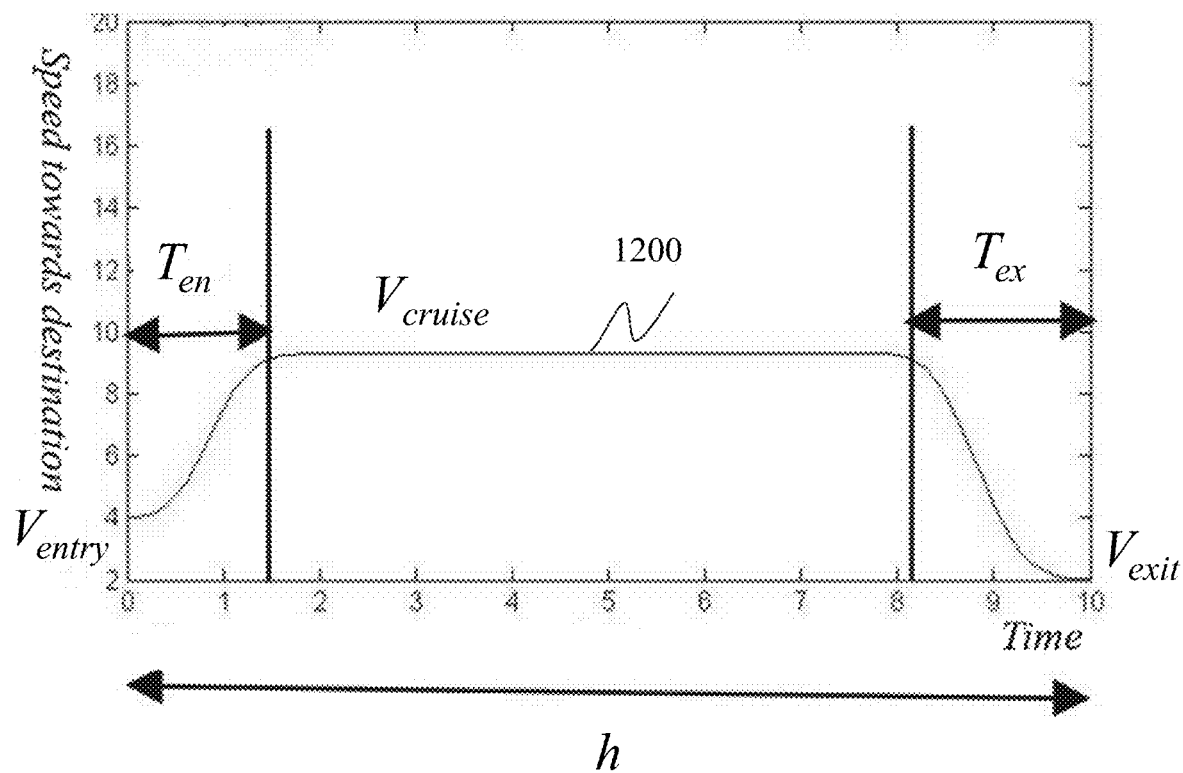
FIG. 12 illustrates an exemplary velocity mode of a component in a segment according to some embodiments of the present disclosure.

FIG. 12 illustrates an exemplary velocity mode of a component in a segment according to some embodiments of the present disclosure. The horizontal axis represents the time or segment time, and the vertical axis represents the velocity (or the speed towards the destination or the ending control node of a segment) of a component. The component may enter the segment at an entry velocity at an entry time point, accelerate from the entry velocity to a cruise velocity in an entry settling time, cruise at the cruise velocity in a cruise time, decelerate from the cruise velocity to an exit velocity in an exit settling time, and exit the segment at the exit velocity at an exit time instant. During this process, the component may need to satisfy a set of constraints. The set of constraints may relate to the velocity, the acceleration, and the jerk of the component. In some embodiments, the velocity of the component may be continuous across the segment according to the constraints. The velocity of the component may be expressed as a piecewise function (10):

$$V(t) = \begin{cases} f(0) = V_{entry}, \dot{f}(0) = 0 & t = T_{entry} \\ f(t - T_{entry}) & T_{entry} < t < T_{entry} + T_{en} \\ f(T_{en}) = V_{cruise} = g(T_{ex}) \text{ and} & T_{entey} + T_{en} < t < T_{exit} - T_{ex}, \\ \dot{f}(T_{en}) = \dot{g}(T_{ex}) = 0 & \\ g(T_{exit} - t) & T_{exit} - T_{ex} < t < T_{exit} \\ g(0) = V_{exit}, \dot{g}(0) = 0, & t = T_{exit} \end{cases} \quad (10)$$

where V(t) denotes a piecewise velocity function of the component across the segment, t denotes time, $T_{entry}$ denotes the time point when the component enters the segment, $T_{en}$ denotes the entry settling time of the component, $T_{ex}$ denotes the exit settling time of the components, $T_{exit}$ denotes the time point when the component leaves the segment, ƒ(t) denotes the left part of the piecewise velocity function V(t), $\dot{f}$(t) denotes the first-order derivate of ƒ(t), g(t) denotes the right part of the piecewise velocity function V(t), $\dot{g}$(t) denotes the first-order derivate of g(t), $V_{entry}$ denotes the entry velocity of the component, $V_{cruise}$ denotes the cruise velocity, and $V_{exit}$ denotes the exit velocity of the component.

In some embodiments, the velocity, the acceleration, and the jerk of the component may be restricted with one or more thresholds. In some embodiments, the one or more thresholds may be set by a user, according to default settings of the radiotherapy system 100, or the like, or a combination thereof. In some embodiments, the one or more thresholds may relate to the structure, the size, or the material of the component. For instance, the velocity, the acceleration, and the jerk of the component may be expressed as formulae (11) through (13):

$$|V(t)| \leq V_{max}, \tag{11}$$

$$|A(t)| = |\dot{V}(t)| \leq A_{max}, \tag{12}$$

$$|J(t)| = |\ddot{V}(t)| \leq J_{max}, \tag{13}$$

where V(t) denotes the velocity function, $\dot{V}(t)$ denotes the first order derivative of the velocity function V(t), $\ddot{V}(t)$ denotes the second order derivative of the velocity function V (t), A(t) denotes the acceleration, J(t) denotes the jerk, $V_{max}$ denotes the maximum velocity, $A_{max}$ denotes the maximum acceleration, and $J_{max}$ denotes the maximum jerk. In some embodiments, $V_{max}$, $A_{max}$, and $J_{max}$ corresponding to a component may be determined according to mechanical structure of the component. In some embodiments, a total duration for the component to traverse the segment may be determined according to formula (14):

$$h = T_{exit} - T_{enter} = T_{en} + T_{cruise} + T_{ex}, \tag{14}$$

where h denotes the total duration for a component to traverse a segment.

In some embodiments, the displacement of the component may be expressed as formula (15):

$$D = \int_{T_{enter}}^{T_{enter}+T_{en}} f(t-T_{enter})dt + V_{cruise} \cdot T_{cruise} + \int_{T_{exit}-T_{ex}}^{T_{exit}} f(T_{exit}-t)dt, \tag{15}$$

when the minimum duration is determined in 706 of the process 700, each component may need to satisfy the constraints set forth as described (e.g., formulae (11) through (15)). More descriptions regarding the exemplary velocity mode may be found in, e.g., U.S. Pub. No. 2017/0354393 A1, the contents of which are incorporated herein by reference.

Figure 13:
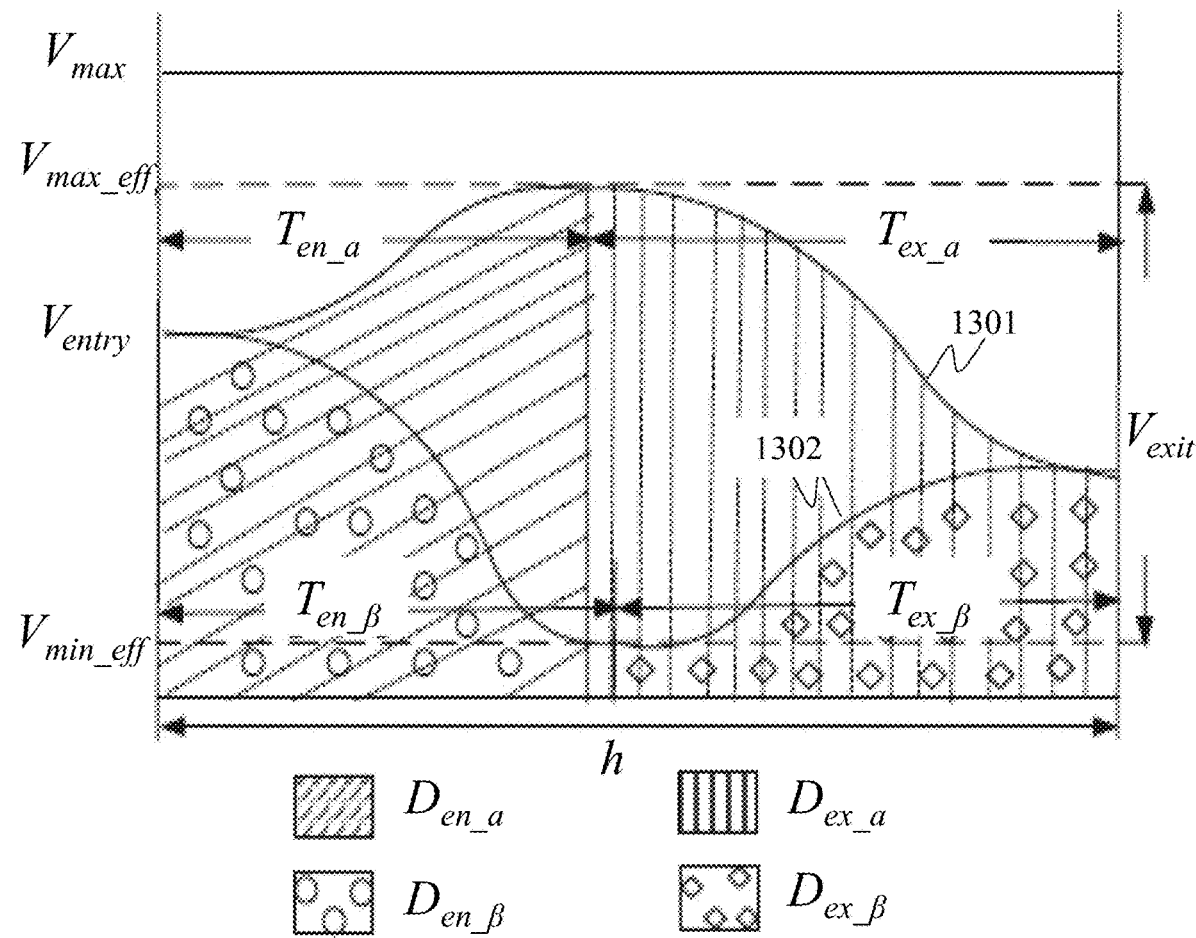
FIG. 13 is a schematic diagram illustrating a maximum effective velocity, a minimum effective velocity, a maximum effective displacement, and a minimum effective displacement of a component in a segment according to some embodiments of the present disclosure.

FIG. 13 is a schematic diagram illustrating a maximum effective velocity, a minimum effective velocity, a maximum effective displacement, and a minimum effective displacement of a component in a segment according to some embodiments of the present disclosure. The horizontal axis represents the time or segment time, and the vertical axis represents the velocity of a component. FIG. 13 may be described in connection with the operations in 808 of the process 800. For a segment defined by a starting control node and an ending control node, the velocities of a component at the starting control node and the ending control node may be an entry velocity $V_{entry}$ and an exit velocity $V_{exit}$, respectively. Given a duration (e.g., a candidate minimum duration) h within which the component needs to traverse the segment, a first velocity curve 1301 and a second velocity curve 1302 may be determined. In some embodiments, the component may also need to satisfy a set of constraints (e.g., formulae (11) through (15)) when the first velocity curve 1301 and the second velocity curve 1302 are determined. The set of constraints may relate to the velocity, the acceleration, the jerk, and/or the displacement of the component in the segment.

The first velocity curve 1301 may include an acceleration stage and a deceleration stage. The acceleration stage may correspond to an acceleration duration $T_{en\_\alpha}$ and an acceleration displacement $D_{en\_\alpha}$, and the deceleration stage may correspond to a deceleration duration $T_{ex\_\alpha}$ and a deceleration displacement $D_{ex\_\alpha}$. A sum of the acceleration duration $T_{en\_\alpha}$ and the deceleration duration $T_{ex\_\alpha}$ may be smaller than or equal to the duration h (i.e., $T_{en\_\alpha}+T_{ex\_\alpha} \leq h$). The peak of the first velocity curve 1301 may be determined as the maximum effective velocity $V_{max\_eff}$. The sum of the acceleration displacement $D_{en\_\alpha}$ and the deceleration displacement $D_{ex\_\alpha}$ may be the maximum effective displacement $S_{max\_eff}$ (i.e., $S_{max\_eff}=D_{en\_\alpha}+D_{ex\_\alpha}$).

The second velocity curve 1302 may include a deceleration stage and an acceleration stage. The deceleration stage may correspond to a deceleration duration $T_{en\_\beta}$ and a deceleration displacement $D_{en\_\beta}$, and the acceleration stage may correspond to an acceleration duration $T_{ex\_\beta}$ and an acceleration displacement $D_{ex\_\beta}$. A sum of the deceleration duration $T_{en\_\beta}$ and the acceleration duration $T_{ex\_\beta}$ may be smaller than or equal to the duration h (i.e., $T_{en\_\beta}+T_{ex\_\beta} \leq h$). The valley of the second velocity curve 1302 may be determined as the minimum effective velocity $V_{min\_eff}$. The sum of the deceleration displacement $D_{en\_\beta}$ and the acceleration displacement $D_{ex\_\beta}$ may be the minimum effective displacement $S_{min\_eff}$ (i.e., $S_{min\_eff}=D_{en\_\beta}+D_{ex\_\beta}$).

In some embodiments, the maximum effective velocity and/or the minimum effective velocity may be determined in a plurality of iterations. For example, the maximum effective velocity of a component may be determined by iteratively checking a difference between the candidate minimum duration corresponding to the segment and an actual duration for the component to traverse the segment with different effective velocities. If the difference between the candidate minimum duration the actual duration is larger than a predetermined threshold (e.g., zero), the effective velocity may be determined as the maximum effective velocity of the component. More descriptions regarding the maximum effective velocity, the minimum effective velocity, the maximum effective displacement, and the minimum effective displacement of a component in a segment may be found in, e.g., U.S. Pub. No. 2017/0354393 A1, the contents of which are incorporated herein by reference.

Figure 14:
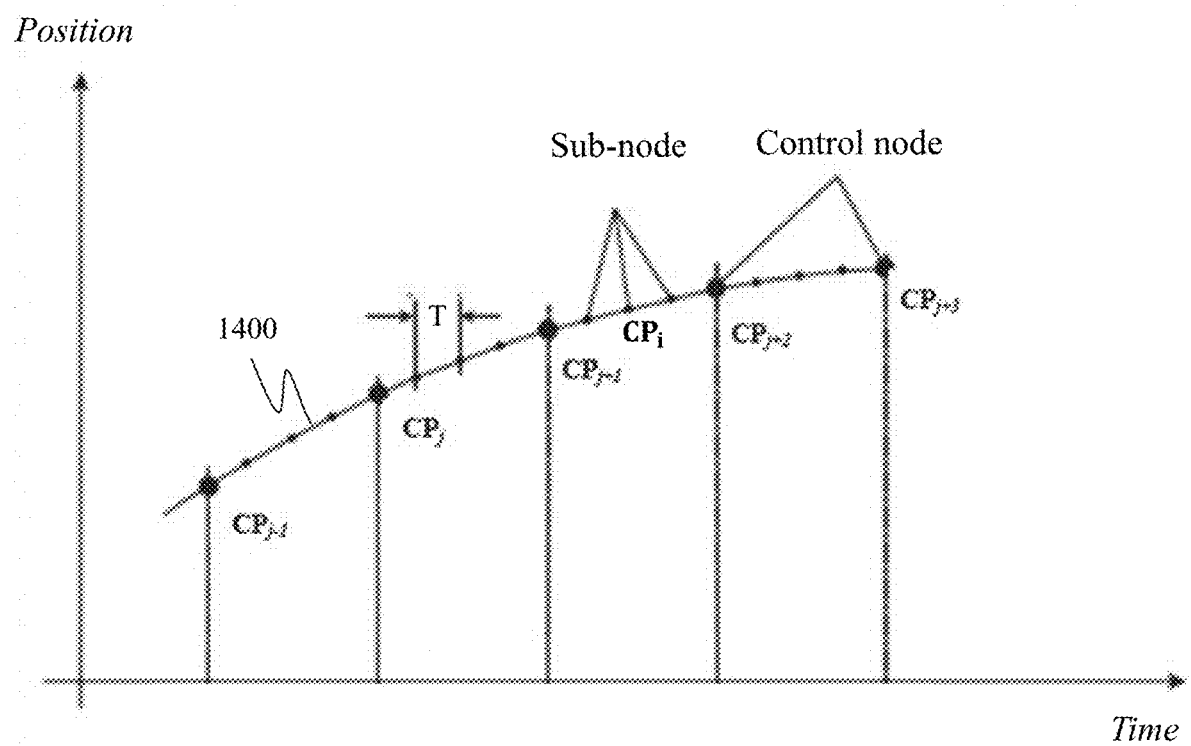
FIG. 14 illustrates exemplary sub-nodes on a trajectory of a component according to some embodiments of the present disclosure.

FIG. 14 illustrates exemplary sub-nodes on a trajectory of a component according to some embodiments of the present disclosure. The horizontal axis represents the time or segment time, and the vertical axis represents the position of a component. In some embodiments, the trajectory 1400 may be generated based on motion parameters of a component determined in 710 of the process 700. The trajectory 1400 may include a plurality of positions corresponding to a plurality of control nodes including, for example, $CP_{j-1}$ through $CP_{j+3}$. In some embodiments, a plurality of sub-nodes may be generated between two sequential control nodes. The plurality of sub-nodes may further divide the segment between the two sequential control nodes into one or more sub-segments. In some embodiments, there may be a regular interval T between two sequential sub-nodes, for example, 2 seconds, 5 seconds, or the like. For example, a segment between the control nodes $CP_{j+1}$ and $CP_{j+2}$ may be divided into four sub-segments by three sub-nodes. A sub-node may include control information for the multiple components. The control information may include a time point when the component reaches the sub-node, a position of the component corresponding to the sub-node, a velocity at the sub-node, an acceleration at the sub-node, or the like. Merely for illustration purposes, the control information for a sub-node $CP_i$ may include a time point $t_i$ when the component arrives at $CP_i$, a position $Pos_i$ corresponding to $CP_i$, a velocity $Vel_i$ at $CP_i$, an acceleration $Acc_i$ at $CP_i$, or the like. The sub-nodes may be used to control the motion of the component when it traverses a segment.

Figure 15:
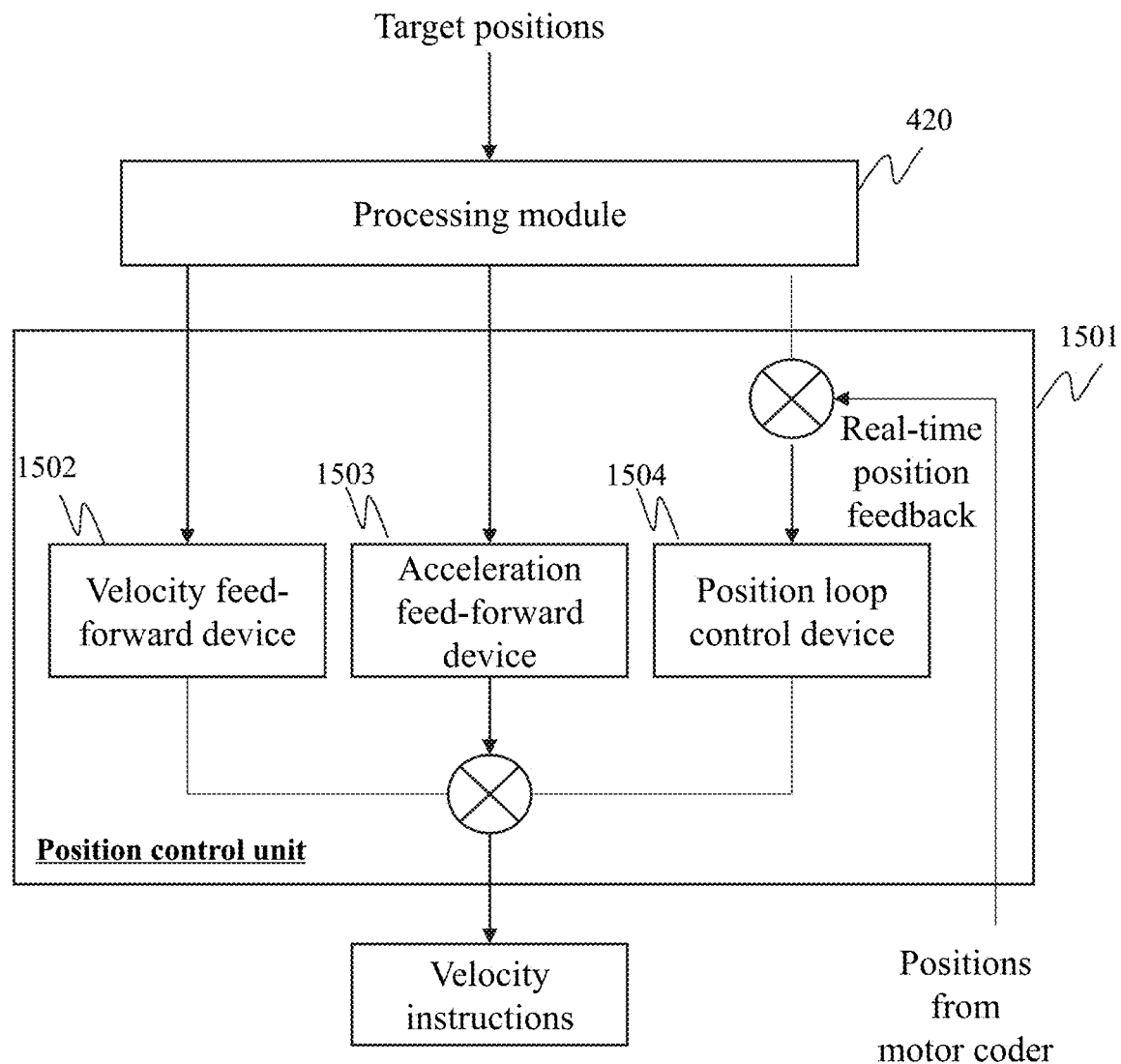
FIG. 15 is a schematic diagram illustrating an exemplary control model for controlling motions of the multiple components according to some embodiments of the present disclosure.

FIG. 15 is a schematic diagram illustrating an exemplary control model for controlling motions of the multiple components according to some embodiments of the present disclosure. The control model may be implemented by one or more modules or devices of the radiotherapy system 100 to facilitate motion control of the multiple components. The processing module 420 may obtain plan data including a plurality of target positions of the multiple components, and generate motion parameters of the multiple components by, for example, performing one or more operations provided with reference to FIG. 7 through FIG. 9. The motion parameters may include, for example, a time point when the component reaches a control node or a sub-node, a position of the component corresponding to the control node or the sub-node, a velocity at the control node or the sub-node, an acceleration at the control node or the sub-node, a cruise velocity between two sequential control nodes or sub-nodes, an acceleration duration for an acceleration stage, etc. Taking a sub-node $Cp_i$ as an example, the sub-node $Cp_i$ may be represented by $Cp_i(t_i, Pos_i, Vel_i, Acc_i)$, where $t_i$ represents the time point when the component arrives at $CP_i$, $Pos_i$ represents a position of the component corresponding to $CP_i$, $Vel_i$ represents a velocity of the component at $CP_i$, and $Acc_i$ represents an acceleration of the component at $CP_i$.

In some embodiments, the radiotherapy system 100 may include a position control unit 1501. In some embodiments, the position control unit 1501 may be a part of the control module 430. The position control unit 1501 may further include a velocity feed-forward device 1502, an acceleration feed-forward device 1503, and a position loop control device 1504. The processing module 420 may transmit information regarding the one or more sub-nodes to the devices in the position control unit 1501 at a predetermined interval (20 milliseconds). The information may include, e.g., position information, velocity information, acceleration information, etc. Taking the sub-node Cp as an example, the position $Pos_i$ may be transmitted into the loop control device 1504 to control positions of the component, the velocity $Vel_i$ may be transmitted into the velocity feed-forward device 1502 to control velocities of the component, and the acceleration $Acc_i$ may be transmitted into the acceleration feed-forward device to control accelerations of the component. In some embodiments, the position loop control device 1504 may receive detected positions of the multiple components from a position detecting device (e.g., a motor coder, a position sensor, an angular position sensor, etc.). The detected positions from the position detecting device may be used as real-time position feedback. Merely for illustration purposes, the position loop control device 1504 may determine whether there is a deviation between the detected position of a component and a position corresponding to a sub-node. If there is a deviation, the velocity feed-forward device 1502 and/or the acceleration feed-forward device 1503 may dynamically adjust the velocity of the component so that the component may timely reach the position corresponding to the sub-node based on the deviation. The velocity feed-forward device 1502, the acceleration feed-forward device 1503, and the position loop control device 1504 may generate velocity instructions about velocities of the multiple components based on the one or more sub-nodes. In some embodiments, the control module may further include a velocity loop (not shown in the figure), which may receive the velocity instructions from the position control unit 1501, and control the motions of the multiple components based on the velocity instructions.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PRP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:

1. A method implemented on at least one computing device, each of which has at least one processor and storage, the method comprising:
    obtaining a plurality of sets of positions of multiple components of an apparatus, the apparatus including a radiotherapy device, each set of positions of the multiple components corresponding to a control node, and two sequential controls defining a segment of at least one segment;
    determining, based on the plurality of sets of positions of the multiple components, a velocity of each component at each control node;
    determining, based on the velocity of each component at each control node, a minimum duration for each component to traverse each segment of the at least one segment;
    determining, based on the minimum duration for each component to traverse each segment of the at least one segment, an optimized duration corresponding to the each segment;
    determining, based on the optimized duration corresponding to each segment, motion parameters of each component in the each segment; and
    delivering, based on the plurality of sets of positions of the multiple components of the apparatus, a radiation dose during the at least one segment.

2. The method of claim 1, the motion parameters being such that the multiple components moving according to the motion parameters arrive at the each set of positions defined by the control node at a same time.

3. The method of claim 1, the multiple components including at least one of a gantry or one or more leaves of a multi-leaf collimator (MLC).

4. The method of claim 1, the motion parameters of each component including at least one of an acceleration duration, a cruise duration, a deceleration duration, or a cruise velocity.

5. The method of claim 1, the determining, based on the plurality of sets of positions of the multiple components, a velocity of each component at each control node including:
    for each component at a current control node,
        determining, based on the plurality of sets of positions of the multiple components, a first displacement between a reference control node and a prior control node;
        determining, based on the plurality of sets of positions of the multiple components, a second displacement between the reference control node and the current control node;
        determining, based on the plurality of sets of positions of the multiple components, a third displacement between the reference control node and a subsequent control node; and
        determining, based on the first displacement, the second displacement, and the third displacement, the velocity of the component at the current control node.

6. The method of claim 5, the determining, based on the first displacement, the second displacement, and the third displacement, the velocity of the component at the current control node including:
  determining that the first displacement, the second displacement, and the third displacement fail to conform to a first monotonic change with time; and
  in response to determining that the first displacement, the second displacement, and the third displacement fail to conform to the first monotonic change with time, designating the velocity of the component at the current control node as zero.

7. The method of claim 5, further comprising:
  determining that the first displacement, the second displacement, and the third displacement conform to a monotonic change with time; and
  in response to determining that the first displacement, the second displacement, and the third displacement conform to the monotonic change with time, designating the velocity of the component at the current control node as non-zero.

8. The method of claim 1, the determining, based on the velocity of each component at each control node, a minimum duration for each component to traverse each segment of the at least one segment including:
  for each component in each segment of the at least one segment,
    obtaining a set of constraints of the component;
    determining, based on the velocity of the component at each control node, a velocity mode of the component; and
    determining, based on the velocity mode and the set of constraints, the minimum duration for the component to traverse the each segment of the at least one segment.

9. The method of claim 1, the determining, based on the minimum duration for each component to traverse each segment of the at least one segment, an optimized duration corresponding to each segment including:
  for the each segment of the at least one segment, determining, based on the minimum duration for each component to traverse the each segment, a candidate minimum duration corresponding to the each segment; and
  determining, based on the candidate minimum duration corresponding to the each segment of the at least one segment, the optimized duration corresponding to the each segment of the at least one segment.

10. The method of claim 9, further including:
  for the each segment of the at least one segment, determining, based on the minimum duration for each component to traverse the each segment, a candidate maximum duration corresponding to the each segment, wherein the candidate maximum duration and the candidate minimum duration constitute a range within which the optimized duration is determined.

11. The method of claim 9, the determining the optimized duration corresponding to the each segment of the at least one segment including:
  determining, based on the candidate minimum duration corresponding to the each segment of the at least one segment, entry velocities of the multiple components at a starting control node and exit velocities of the multiple components at an ending control node of the each segment of the at least one segment;
  determining, based on the entry velocities and the exit velocities in the segment, maximum effective displacements each of which corresponds to one of the multiple components in the segment;
  determining, based on the plurality of sets of positions of the multiple components, displacements of the multiple components in the segment; and
  determining, based on the maximum effective displacements and the displacements of the multiple components, the optimized duration corresponding to the segment.

12. The method of claim 11, the determining the optimized duration corresponding to the segment including:
  determining that each of the displacements of the multiple components is smaller than a corresponding maximum effective displacement of the maximum effective displacements; and
  in response to determining that each of the displacements of the multiple components is smaller than a corresponding maximum effective displacement of the maximum effective displacements, designating the candidate minimum duration as the optimized duration for the segment.

13. The method of claim 12, the determining that each of the displacements of the multiple components is smaller than a corresponding maximum effective displacement of the maximum effective displacements further including:
  determining that each of the displacements of the multiple components is between the corresponding maximum effective displacement and a corresponding minimum effective displacement, wherein the corresponding minimum effective displacement is a displacement that one of the multiple components reaches within the candidate minimum duration.

14. The method of claim 11, the determining the optimized duration corresponding to the segment including:
  determining that the displacement of each of at least one component of the multiple components is larger than the corresponding maximum effective displacement of the each of the at least one component; and
  in response to determining that the displacement of each of the at least one component is larger than the corresponding maximum effective displacement, updating the candidate minimum duration corresponding to the segment in one or more iterations, each of the one or more iterations further including:
  updating the candidate minimum duration based on the displacements of the multiple components, the minimum effective displacements of the multiple components, and the maximum effective displacements of the multiple components.

15. The method of claim 14, further including:
  identifying one or more components from the multiple components, wherein each of the one or more iterations for determining the optimized duration is performed with respect to the identified one or more components prior to other components of the multiple components that are different from the identified one or more components.

16. The method of claim 15, the identified one or more components including:
  a first component with a larger minimum duration compared to the other components of the multiple components;
  a first leaf of an MLC with a larger displacement in a first motion mode compared to the other components of the multiple components;

a second leaf of the MLC with a larger displacement in a second motion mode compared to the other components of the multiple components; and a third leaf of the MLC with a larger displacement in a third motion mode compared to the other components of the multiple components.

17. The method of claim 16, further including:

in response to determining that at least one of the displacements of the identified one or more components is larger than the maximum effective displacement, determining the optimized duration corresponding to another segment occurred prior to the segment.

18. The method of claim 11, the determining the optimized duration corresponding to the each segment including:

performing the determination of the optimized duration for a second segment after the optimized duration for a first segment is determined, the first segment being prior to the second segment.

19. A system comprising:

a storage device storing a set of instructions; and at least one processor configured to communicate with the storage device, wherein when executing the set of instructions, the at least one processor is configured to cause the system to:

obtain a plurality of sets of positions of multiple components of an apparatus, the apparatus including a radiotherapy device, each set of positions of the multiple components corresponding to a control node, and two sequential controls defining a segment of at least one segment;

determine, based on the plurality of sets of positions of the multiple components, a velocity of each component at each control node;

determine, based on the velocity of each component at each control node, a minimum duration for each component to traverse each segment of the at least one segment;

determine, based on the minimum duration for each component to traverse each segment of the at least one segment, an optimized duration corresponding to the each segment;

determine, based on the optimized duration corresponding to each segment, motion parameters of each component in the each segment; and deliver, based on the plurality of sets of positions of the multiple components of the apparatus, a radiation dose during the at least one segment.

20. A non-transitory computer-readable medium storing instructions, the instructions, when executed by a computing device, cause the computing device to:

obtain a plurality of sets of positions of multiple components of an apparatus, the apparatus including a radiotherapy device, each set of positions of the multiple components corresponding to a control node, and two sequential controls defining a segment of at least one segment;

determine, based on the plurality of sets of positions of the multiple components, a velocity of each component at each control node;

determine, based on the velocity of each component at each control node, a minimum duration for each component to traverse each segment of the at least one segment;

determine, based on the minimum duration for each component to traverse each segment of the at least one segment, an optimized duration corresponding to the each segment;

determine, based on the optimized duration corresponding to each segment, motion parameters of each component in the each segment; and deliver, based on the plurality of sets of positions of the multiple components of the apparatus, a radiation dose during the at least one segment.

* * * * *